(12) United States Patent
Schneiker et al.

(10) Patent No.: US 6,815,688 B2
(45) Date of Patent: Nov. 9, 2004

(54) DEVICES FOR GUIDING AND MANIPULATING ELECTRON BEAMS

(76) Inventors: Conrad W. Schneiker, 996 Meridian Ave., Apt 64, San Jose, CA (US) 95126; Robert Gray, 180 Poplar St. #4, Rochester, NY (US) 14620

( * ) Notice: Subject to any disclaimer, the term of this patent is extended or adjusted under 35 U.S.C. 154(b) by 0 days.

(21) Appl. No.: 10/615,499

(22) Filed: Jul. 8, 2003

(65) Prior Publication Data
US 2004/0061051 A1 Apr. 1, 2004

Related U.S. Application Data

(63) Continuation-in-part of application No. 10/042,795, filed on Jan. 9, 2002, now Pat. No. 6,700,127.
(60) Provisional application No. 60/394,379, filed on Jul. 8, 2002.

(51) Int. Cl.[7] ............................ G21K 7/00; G01N 23/00
(52) U.S. Cl. ................ 250/396 R; 250/313; 250/361.1
(58) Field of Search ............................ 250/396 R, 313, 250/361.1

(56) References Cited

FOREIGN PATENT DOCUMENTS

JP         401033836     *   7/1989

OTHER PUBLICATIONS

Matsuzawa et al. "High Tc bulk superconductor wigglers", Applied Physics Letters, vol. 59, No. 2, Jul. 8, 1991, 141–142.*

* cited by examiner

*Primary Examiner*—John R. Lee
*Assistant Examiner*—James J. Leybourne
(74) *Attorney, Agent, or Firm*—John M. Hammond; Howard J. Greenwald P.C.

(57) ABSTRACT

A device for guiding a charged particle beam comprising a first superconducting nano-channel. In one embodiment, the device comprises a superconducting nano-channel consisting essentially of a superconducting material in the form of a tube having a proximal end, a distal end, and a bend disposed between said proximal end and said distal end. In another embodiment, the device is formed by a substrate, a first area of superconducting material coated on the substrate and having a first edge, a second area of superconducting material coated on the substrate and having a second edge, the first edge of the first area of superconducting material and the second edge of the second area of superconducting material are substantially parallel. In another embodiment, the device comprises a superconducting nano-channel formed by a plurality of nano-scale superconducting rods disposed around a central region.

24 Claims, 19 Drawing Sheets

DEVICES FOR GUIDING AND MANIPULATING ELECTRON BEAMS

CROSS-REFERENCE TO RELATED PATENT APPLICATIONS

This application is a continuation-in-part of application Ser. No. 10/042,795 filed Jan. 9, 2002, now U.S. Pat. No. 6,700,127 and further claims the benefit of the filing date of U.S. provisional patent application Ser. No. 60/394,379, filed Jul. 8, 2002.

This invention relates generally to carbon-based nanotube probes for microscopy devices, and particularly to superconducting nano-channels for guiding and manipulating electron beams or other charged particles.

FIELD OF THE INVENTION

Carbon-based nanotube probes for microscopy devices, and superconducting nano-channels for guiding and manipulating electron beams or other charged particles in particular.

BACKGROUND OF THE INVENTION

Many analytical devices, such as electron microscopes, are used to image the topography and surface properties of a substrate. These devices utilize a focused beam of electrons to illuminate a substrate. Sources of these electron beams are often contained in the tips of the analytical device.

Electron point sources, which may be utilized in these analytical devices, are well known. These electron point sources, often on the order of the atomic scale and adapted to provide field emission of coherent electron beams, have been described in, e.g., "Coherent point source electron beams", Hans-Werner Fink, Werner Stocker, and Heinz Schmid, Journal of Vacuum Science and Technology B, Volume 8, Number 6, Nov/Dec 1990, pp. 1323–1324, in "Unraveling nanotubes: field emission from an atomic wire," A. G. Rinzler, J. H. Hafner, P. Nikolaev, L. Lou, S. G. Kim, D. Tomanek, P. Nordlander, D. T. Colbert and R. E. Smalley, Science, 269, pp. 1550–1553 (1995), and in "Carbon nanotubes are coherent electron sources", Heinz Schmid, Hans-Werner Fink, Applied Physics Letters, Volume 70, Number 20, 19 May 1997, pp. 2679–2680. The first reference discloses a tungsten tip terminated with an atomically perfect pyramid of tungsten atoms as the electron emitter. The second and third references disclose a carbon nanotube as the electron emitter.

By way of further illustration, U.S. Pat. No. 5,654,548 ("Source for intense coherent electron pulses") discloses how such sources can be used for one type of electron microscopy. The entire disclosure of this United States patents is hereby incorporated by reference into this specification.

Electron beams have been used in constructing microscopes. For example, U.S. Pat. No. 6,005,247 (Electron beam microscope using electron beam patterns) discloses "An electron beam microscope includes an electron beam pattern source, a vacuum enclosure, electron optics, a detector and a processor." U.S. Pat. No. 6,043,491 (Scanning electron microscope) discloses "A scanning electron microscope in the present invention, by employing a retarding method and suppressing interferences between an electron beam and secondary electrons or back scattered electrons, makes it possible to obtain a clearer SEM image with a higher resolution." The entire disclosure of each of these United States patents is hereby incorporated by reference into this specification.

Field emitted electron beams are also useful in many types of vacuum microelectronic devices, as described in "Vacuum Microelectronics," edited by Wei Zhu, (John Wiley & Sons, New York, 2001).

Fabrication of specialized tips used in scanning electron microscopes and atomic force microscopes is well known to those skilled in the arts. For example, U.S. Pat. No. 6,020,677 (Carbon cone and carbon whisker field emitters) discloses "Carbon cone and carbon whisker field emitters are disclosed. These field emitters find particular usefulness in field emitter cathodes and display panels utilizing said cathodes." U.S. Pat. No. 5,393,647 (Method of making superhard tips for micro-probe microscopy and field emission) discloses "Forming micro-probe tips for an atomic force microscope, a scanning tunneling microscope, a beam electron emission microscope, or for field emission, by first thinning a tip of a first material, such as silicon." The entire disclosure of each of these United States patents is hereby incorporated by reference into this specification.

The prior art sources of atomic point source electron beam emitters typically must be operated at very low pressures, on the order of about 10-8 to 10-10 Torr, to protect them from disruptive contamination, chemical degradation, or destructive ion bombardment by residual gas ions. This often requires the use of complicated, expensive, and cumbersome equipment.

Carbon-based nanotubes may be configured as superconducting nano-channels. Nanotubes are resilient and have nanometer-scale, sharp tips. As such, they are useful for making micro-probe tips of microscopy devices, e.g., scanning tunneling microscope and atomic force microscope. The dimensions of carbon-based nanotubes, ideally having a single atom at the tip apex, but typically being 3 to 10 atoms in diameter at the tip, allows the tip to be positioned close enough to a conducting substrate so that a tunneling current flows between the tip and the substrate under an applied bias voltage. This tunneling current is similar to the tunneling of electrons across a barrier as described by the Josephson tunneling effect, which is obtained from a system comprising two layers of superconductive material separated by a barrier. The two layers are either connected by a very narrow conductive bridge, or are separated by a layer of nonconductive material. When this system is under superconducting conditions (low temperature), a tunneling effect takes place, in which a superconducting current or super current flows across the barrier between the superconductive layers.

In the case of carbon-based superconducting nanotubes, the barrier is the repulsive force of the Meissner effect between the superconducting carbon-based nanotube and substrate. The Meissner effect is the ability of a material in a superconducting state to expel all magnetic fields therefrom (i.e., such a superconductor is perfectly diamagnetic and exhibits a permeability of zero). Reference may be had to "The Further Inventions of Daedalus", by David E. H. Jones, Oxford Press, 1999. In the section relating to "Electric Gas Light on Tap" (pages 174–175) the author describes methods for exploiting the Meissner effect of evacuated superconducting tubes for purposes of residential electric beam-based power distribution. Further reference may be had, e.g., to U.S. Pat. No. 4,975,669 (Magnetic bottle employing Meissner effect). The entire disclosure of this United States patent is hereby incorporated by reference into this specification. Atomic force microscopes, which rely on the repulsive force generated by the overlap of the electron cloud at the tip's surface with electron clouds of surface atoms within the substrate, negate the need of conducting substrates to obtain the same effect.

As used herein, the term "nanotube" refers to a hollow structure having a diameter of from about 0.3 to about 10 nanometers, and a, length of from about 3 to about 10,000 nanometers. In general, such nanotubes have aspect ratios of at least about 1:10 to about 1:1000. Carbon-based nanotubes are hollow structures composed between 95-to100% of carbon atoms. In general, the most commonly studied forms of nanotubes have physical properties such that they conduct electricity better than copper. Typically, carbon nanotubes have tensile strength 100 times that of steel. Carbon nanotubes become superconductors at very low temperatures. Nanotubes may be fabricated from materials other than carbon, e.g., Tungsten disulphide, Molybdenum disulphide, and Boron nitride. Carbon nanotubes may be capped with metallic cores. Carbon nanotubes can be doped with other elements, e.g. metals.

Carbon-based nanotubes may be either single-walled nanotubes (SWNT) or multi-walled nanotubes (MWNT). A MWNT includes several nanotubes each having a different diameter. Thus, the smallest diameter nanotube is encapsulated by a larger diameter nanotube, which in turn, is encapsulated by another larger diameter nanotube. Carbon-based nanotubes are used to form superconducting nanochannels for steering and channeling very fine electron beams or other charged particles. In order to preserve near perfect vacuum and ultra-clean conditions, the outlet ends of the superconducting nanochannels are sealed with electron transparent nano-membranes.

Fabrication of specialized tips comprising carbon-based nanotubes and its use in scanning electron microscopes and atomic force microscopes is well known to those skilled in the arts. For example, U.S. Pat. No. 6,020,677 (Carbon cone and carbon whisker field emitters) discloses "Carbon cone and carbon whisker field emitters. These field emitters find particular usefulness in field emitter cathodes and display panels utilizing said cathodes." U.S. Pat. No. 5,393,647 (Method of making super hard tips for micro-probe microscopy and field emission) discloses "Forming micro-probe tips for an atomic force microscope, a scanning tunneling microscope, a beam electron emission microscope, or for field emission, by first thinning a tip of a first material, such as silicon." The entire disclosure of each of these United States patents is hereby incorporated by reference into this specification.

Electron transparent nano-membranes are well known to those skilled in the art. Reference may be had, e.g., to U.S. Pat. Nos. 6,300,631 (Method of thinning an electron transparent thin film membrane on a TEM grid using a focused ion beam), 6,194,720 (Preparation of transmission electron microscope samples), 6,188,068, 6,140,652, 6,100,639, 6,060,839, 5,986,264, 5,940,678 (Electronic transparent samples), 5,633,502, 4,680,467, 3,780,334 (Vacuum tube for generating a wide beam of fast electrons), and the like. The entire disclosure of each of these United States patents is hereby incorporated by reference into this specification.

The prior art sources of carbon-based nanotube applications for microscopy devices typically consist of attaching a carbon-based nanotube to the tip of a microscopy probe. The prior art, however, does not include microscopy probes incorporating superconducting nano-channels comprising carbon-based nanotubes, which are capable of guiding and manipulating charged particle beams for microscopy applications. In the remainder of this specification reference will be made to the use of single walled superconducting carbon nanotubes. However, it is to be understood that multi-walled superconducting carbon nanotubes may be utilized as well, as may be any other essentially atomically perfect nanotube structure, which, if not naturally superconducting, may be optionally externally coated with a thin film of superconducting material.

It is an object of this invention to provide superconducting nanochannels structures configured for guiding and manipulating electron beams or other charged particles. The superconducting nanochannels of this invention comprise carbon-based nanotubes, and may be used to fabricate nanometer scale tips for a microscopy probe.

SUMMARY OF THE INVENTION

In accordance with the present invention, there is provided a device for guiding a charged particle beam comprising a superconducting nano-channel consisting essentially of a superconducting material in the form of a tube having a proximal end, a distal end, and a bend disposed between said proximal end and said distal end.

In accordance with the present invention, there is further provided a device for guiding a charged particle beam comprising a first superconducting nano-channel formed by a substrate, a first area of superconducting material coated on said substrate and having a first edge, a second area of superconducting material coated on said substrate and having a second edge, wherein said first edge of said first area of superconducting material and said second edge of second area of superconducting material are substantially parallel.

In accordance with the present invention, there is further provided a device for guiding a charged particle beam comprising a superconducting nano-channel formed by a plurality of nano-scale superconducting rods disposed around a central region.

In accordance with the present invention, there is further provided a device for guiding a charged particle beam comprising a superconducting nano-channel comprising a first split and a second split disposed parallel to the central axis of said nano-channel, said first and second splits forming a first section and a second section of said nano-channel.

BRIEF DESCRIPTION OF THE DRAWINGS

The invention will be described by reference to the following drawings, in which like numerals refer to like elements, and in which.

Figure 1:
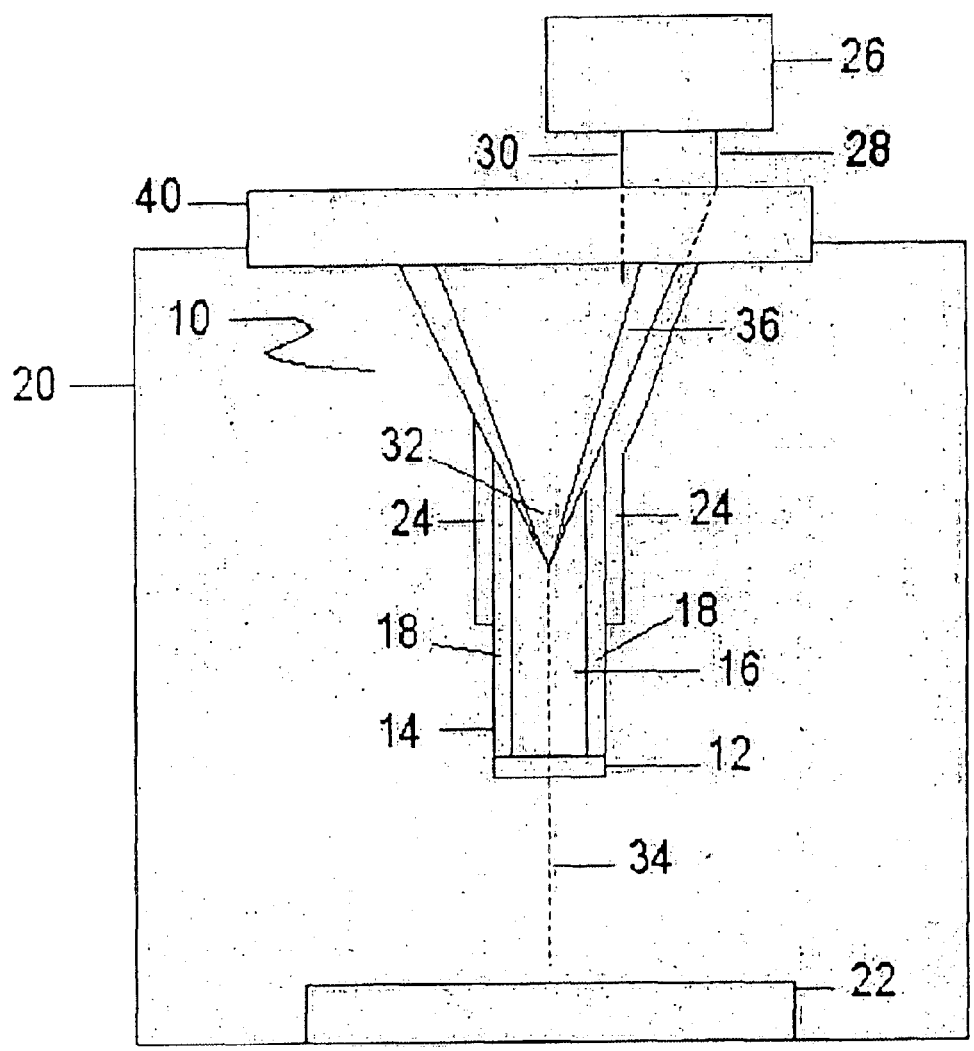
FIG. 1 is a schematic representation of an enclosed point source electron beam generator.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

For a general understanding of the present invention, reference is made to the drawings. In the drawings, like reference numerals have been used throughout to designate identical elements. In describing the present invention, a variety of terms are used in the description. As used herein unless otherwise specified, the term electron beam as used throughout this specification is meant to include any beam comprising charged particles as is known to those skilled in the art.

Atomic scale point source electron beams have many potential advantages for scanning electron microscopy, including higher resolution at lower voltages in much more compact configurations; these electron beam sources also are advantageously used in vacuum microelectronic devices. The primary disadvantage is the requirement for operation at ultra-high vacuum when used as electron field emitters to avoid damage by ion bombardment. By using a miniature ultra-high vacuum chamber to permanently enclose the field emission part, the vacuum requirements for the rest of a scanning electron microscope can be greatly relaxed, leading to major operational and economic advantages, and a much wider range of practical application of this uniquely advantageous point source of coherent electron beams.

In one embodiment, the invention of this patent application comprises the structure and utilization of a monoatomic tip in place of conventional field emission sources, providing a far superior initial electron beam in terms of narrow beam divergence and narrow energy spread and greatly reducing the requirements for high beam voltages and expensive electron optical systems needed for very high resolution imaging.

The enclosed point source electron beam generator described in this specification may operate with a miniature ultra-high vacuum enclosure with an electron-transparent window. This enables the rest of the system to be operated under more conventional vacuum conditions. The rest of the system may comprise conventional or, due to the very narrow electron beam sources produced at relatively low voltages, greatly miniaturized versions of conventional scanning electron microscopes, scanning transmission microscopes, point projection Fresnel microscopes, electron beam lithography systems, and vacuum microelectronic devices.

An alternative means of generating very fine electron beams at low voltages (about 50 to 500 volts) from a conventional electron beam and coupling it to a superconducting nano-channel is also disclosed. Such beams can be used for the microscopy systems and vacuum microelectronic devices.

Very fine electron beams from any of the above sources may be guided and/or manipulated by superconducting nano-channels.

As is known to those in the field of electron beam technology, suitably oriented magnetic fields may be used to confine electron beams for some distance once they have been suitably created and formed. The small size of the electron beam source of this invention and the ability to position it close to the ultimate target makes it feasible to wholly immerse the entire source-to-target system in the bore of a powerful magnetic field generating system whose internal magnetic field is oriented parallel to the main electron beam axis. The magnetic field system, depending on system size and performance requirements, may employ permanent magnets or conventional electromagnets or superconducting electromagnets, optionally augmented with magnetic pole pieces, following common practices well known to those in the art. Immersing the entire system in this magnetic field has the net effect of causing electrons that would normally radially diverge from the main beam axis to instead spiral around it. For scanning electron microscopy or scanning electron beam surface modification applications, either the source or target would need to be mechanically scanned relative to the other. Such scanning may for instance be implemented by any of the lateral electro-mechanical scanning techniques that are used for scanning tunneling microscopes or atomic force microscopes, following common practices well known to those in the field.

In the remainder of this specification reference will be made to the use of single walled superconducting carbon nanotubes. However, it is to be understood that multi-walled superconducting carbon nanotubes may be utilized as well, as may be any other essentially atomically perfect nanotube structure, which, if not naturally superconducting, may be optionally externally coated with a thin film of superconducting material.

In the preferred embodiment illustrated in FIG. 1, there is illustrated a tip assembly 10 comprised of a high quality electron-transparent thin wall 12 positioned at the distal end 14 of an ultra-high vacuum chamber 16.

The thin wall 12 is electron-transparent, i.e., electron beams may be passed through it without significant dispersion or attenuation, relative to the intended application. Electron transparency is a function of electron energy and the type and thickness of the thin wall material. Using means well known to those skilled in the art, the initial electron beam energy would be set for attaining an acceptable level of electron transparency for a particular thin wall material, and then, if needed, the electron beam energy would subsequently be raised or lowered as appropriate for the intended application.

Electron-transparent thin-walls and structures and materials comprising them are well known to those skilled in the art. Reference may be had, e.g., to U.S. Pat. Nos. 6,300,631 (Method of thinning an electron transparent thin film membrane on a TEM grid using a focused ion beam), 6,194,720 (Preparation of transmission electron microscope samples), 6,188,068, 6,140,652, 6,100,639, 6,060,839, 5,986,264, 5,940,678 (electronic transparent samples), 5,633,502, 4,680,467, 3,780,334 (Vacuum tube for generating a wide beam of fast electrons), and the like. The entire disclosure of each of these United States patents is hereby incorporated by reference into this specification.

Referring again to FIG. 1, and in the embodiment depicted, wall 12 is preferably a film that preferably has a thickness of from about 1 to about 50 nanometers. In one preferred embodiment, film 12 consists essentially of silicon nitride, boron nitride, or diamond.

The wall 12, in combination with wall 18, defines a chamber 16. The vacuum within chamber 16 is preferably greater than about $10^{-7}$ Torr. In one aspect of this embodiment, the vacuum within chamber 16 is from about $10^{-7}$ to about $10^{-10}$ Torr.

The vacuum within chamber 16 may be created by conventional means. In one embodiment, (not shown) the tip assembly 10 is placed within an ultra high vacuum chamber (not shown) during its manufacturing assembly process and chamber 16 is vacuum sealed to the electron transparent wall 12 thus enclosing an ultra high vacuum within chamber 16.

The chamber 16 has a relatively small volume, of preferably less than about 1 cubic millimeter. In one embodiment, the chamber 16 has a volume of less than about 0.1 cubic millimeters.

Referring again to FIG. 1, it will be seen that the tip assembly 10 is utilized within a sample vacuum chamber 20 whose volume may be at least about 1,000 times as great as the volume of chamber 16. However, the vacuum in chamber 20 may be substantially lower than the vacuum in chamber 16. The pressure in chamber 20 is typically at least about 10 to 1,000 times as great as the pressure within chamber 16.

Referring again to FIG. 1, and in the preferred embodiment depicted therein, the tip assembly 10 is disposed above sample 22 and can be moved, by means described elsewhere in this specification, so that it is closer to or further away from sample 22.

Referring again to FIG. 1, and in the preferred embodiment depicted therein, an extraction electrode assembly 24 is preferably disposed around chamber 16. Electrode assembly 24 is electrically connected to external voltage supply 26 by means of conductors 28 and 30.

In another embodiment, not shown, the extraction electrode assembly 24 is disposed within chamber 24.

In one embodiment, the extraction electrode assembly 24 is electrically charged to an electrical potential typically in the range 50 to 500 volts with respect to the field emission tip 32 (which is the mono-atomic point source of electron beam 34).

In the embodiment depicted in FIG. 1, tip assembly 10 may comprise either a single or multi walled carbon nanotube 32 or a tungsten mono-atomic point emitter (not shown). Reference may be had to U.S. Pat. Nos. 6,159,742 (Nanometer-scale microscopy probes), 4,939,363 (Scanning tunneling microscope), and the like. The entire disclosure of each of these United States patents is hereby incorporated by reference into this specification.

The extraction electrode assembly 24 may optionally be fashioned from a superconducting material to take advantage of the Meissner effect for narrowing the emission cone of electrons from the emitter due to the superconducting material's expulsion and thus confinement of the magnetic fields of the emerging electrons. The Meissner effect is the ability of a material in a superconducting state to expel all magnetic fields therefrom (i.e., such a superconductor is perfectly diamagnetic and exhibits a permeability of zero). Reference may be had, e.g., to U.S. Pat. No. 4,975,669 (Magnetic bottle employing Meissner effect). The entire disclosure of this United States patent is hereby incorporated by reference into this specification.

Referring again to FIG. 1, and in the preferred embodiment depicted therein, the emission tip 32 is attached to an electrically insulating tip enclosure 36 to isolate the tip 32 from electrode 24. An electrical connection is made from the voltage source 26 to the electrode 24 by means of conductor 28. An electrical connection is made from the voltage source 26 to the tip 32 by means of conductor 30. The entire assemblage is attached to an electrically insulating supporting mount 40.

In this preferred embodiment, the beam extraction voltage preferably is selected according to the type of ultra thin film material used for the electron window 12, since, as is known to those skilled in the arts, transparency is energy dependent. After passage through the electron window 12, the beam 34 can subsequently be accelerated or decelerated as needed to a target-relative voltage in the range of about 20 to 1,000 volts.

Figure 2:
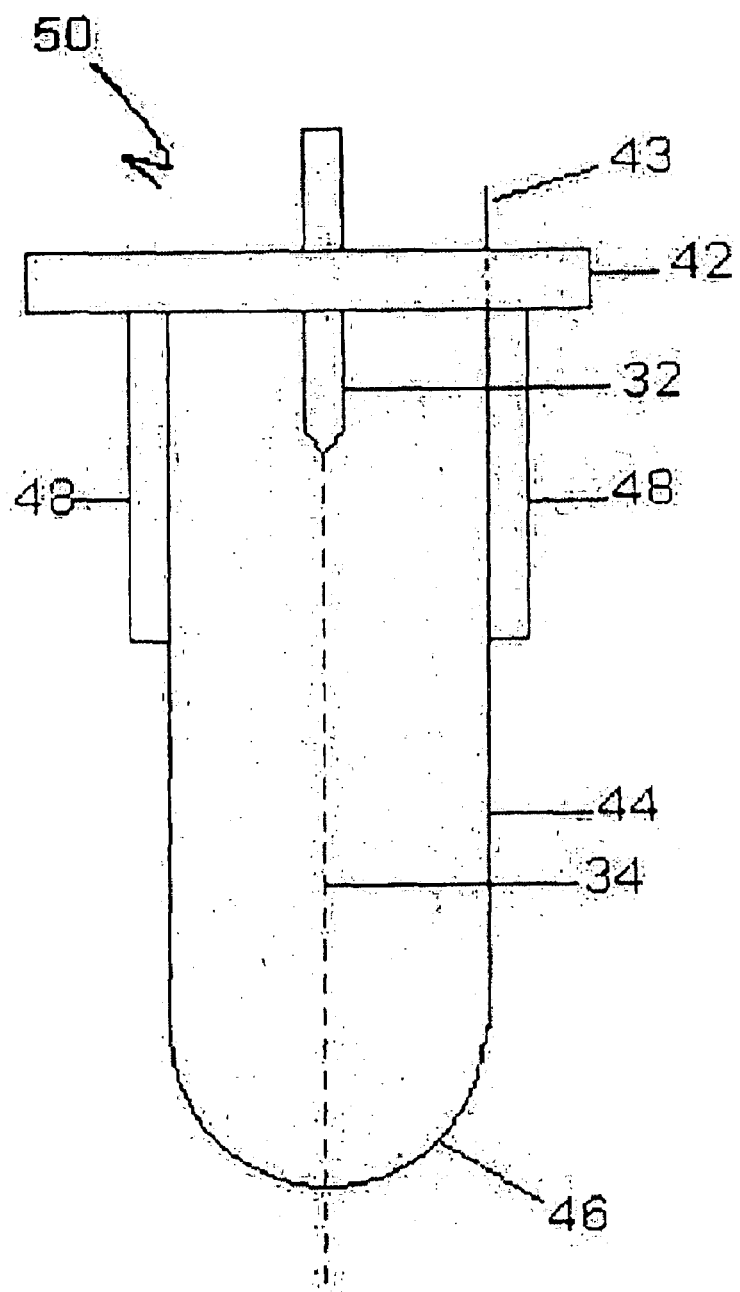
FIG. 2 is a schematic representation of an enclosed point source electron beam generator.

FIG. 2 illustrates another configuration of a tip assembly 50 in which tip 32 is in the shape of a carbon nanotube. In this embodiment, tip 32 has a relatively small diameter, in the range of 0.3 to 10 nanometers. In this embodiment, the carbon nanotube may be composed of single or multi-walled metallic-type carbon nanotube; alternatively, it may be composed of tungsten mono-atomic point emitter or other suitable material.

Referring again to FIG. 2, the tip 32 is preferably embedded in a support structure 42, which also serves as a thermal sink and ultra-high vacuum seal to a superconducting single walled metallic-type carbon nanotube 44 of relatively larger diameter (in the range, e.g., of approximately 5 to 200 nanometers), which also serves as a field emission extraction electrode and as a miniature ultra-high vacuum chamber. Electrical lead 43 passes through the support structure 42 to provide a means for creating an electrical potential difference between tip 32 and wall 44. In this embodiment, the electron beam 34 emerges from the field emitter 32 and is confined and focused by the superconducting nanotube 44. Since the momentum of the electrons in beam 34 is largely parallel to the wall 44, relatively little force is required to confine it within wall 44. This beam penetrates and emerges from the semispherical end cap 46. This end cap is less strongly superconducting, or may not be superconducting at all, than the rest of the carbon nanotube 44. Since the momentum of the electron beam 34 is perpendicular to the middle of end cap 46, the middle of end cap 46 serves as an electron window for certain material-dependent electron beam energies. An optional coating of material 48, which may optionally be superconducting, may be used for purposes of vacuum sealing, enhanced mechanical strength, or enhanced superconducting focusing of electron beam 34. In another embodiment (not shown), coating 48 may be connected to the electrical lead 43 and is then used as an electron extraction electrode, instead of nanotube 44.

Figure 3:
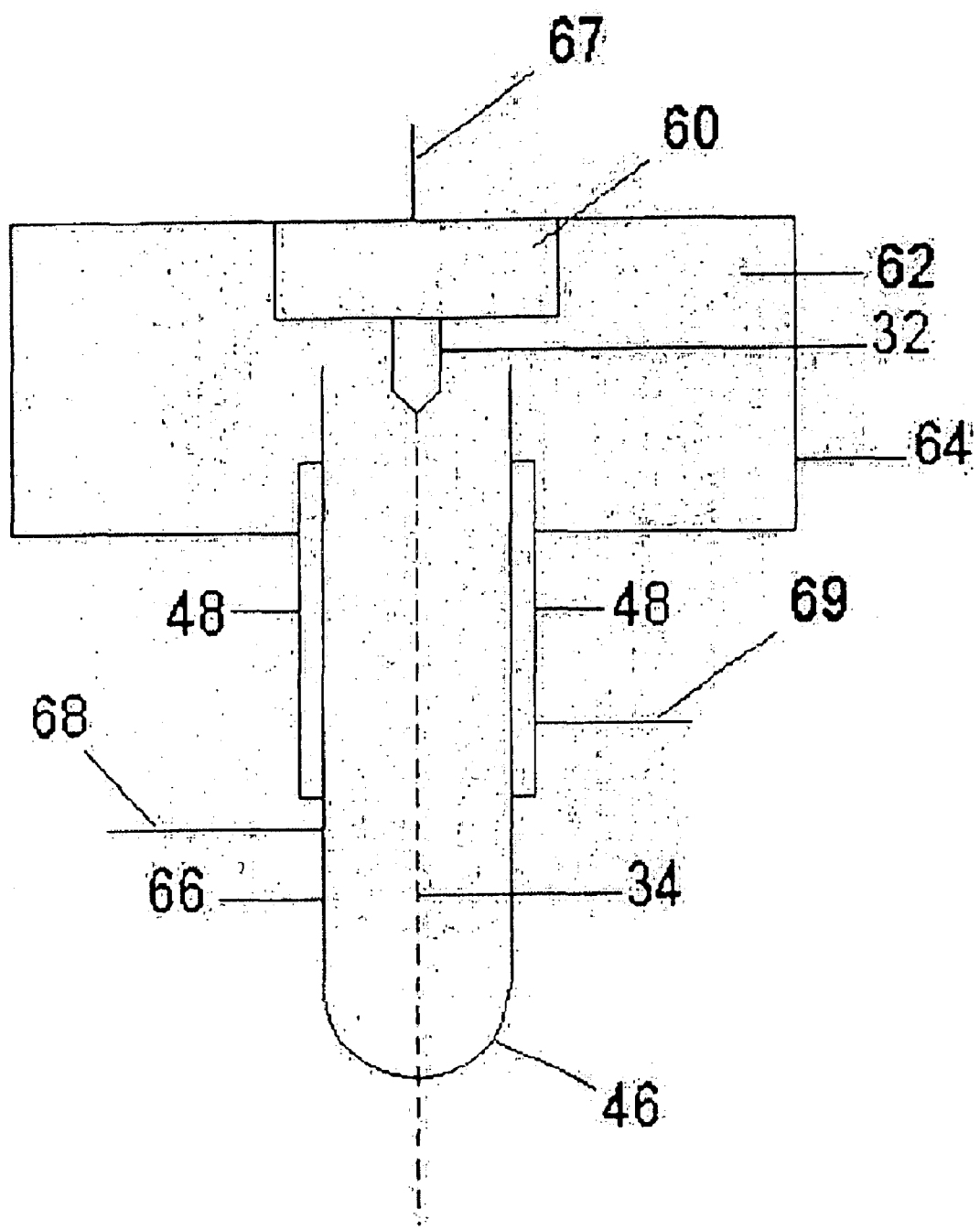
FIG. 3 is a schematic representation of an enclosed point source electron beam generator.

FIG. 3 illustrates another preferred embodiment of this invention. In this configuration, a fixed or dynamic emitter tip positioning system 60 is enclosed in a miniature ultra high vacuum chamber 62 and support structure 64. The tip 32 preferably has a relatively small diameter, e.g. in the range of approximately 0.3 to 10 nanometers; single walled metallic-type carbon nanotube 32 serves as an atomic point source field emitter of electrons 34. Alternatively, the atomic point source field emitter 32 may be a multi-walled carbon nanotube or a tungsten mono-atomic point emitter or other suitable material. This electron emitter 32 is embedded in a positioning system 60. The support structure 64 also serves as a thermal sink and ultra-high vacuum seal to a superconducting single walled metallic-type carbon nanotube 66 of relatively larger diameter, e.g. in the range of approximately 5 to 200 nanometers, which serves both as a field emission extraction electrode and as a miniature ultra-high vacuum chamber.

The electron beam 34 emerges from the field emitter 32 and is confined and focused by the superconducting nanotube 66. The electron beam 34 penetrates the semispherical end cap 46 and emerges from the end of it. This end cap is less strongly superconducting or may not be superconducting at all. Since the momentum of the electron beam is perpendicular to the end cap 46 it serves as an electron window. An optional coating of material 48, optionally superconducting, may be used for purposes of vacuum sealing, enhanced mechanical strength, or enhanced superconducting focusing of the electron beam.

In the embodiment depicted in FIG. 3, electrical leads 67, 68 are connected to a voltage supply (not shown) which provides the electrical potential difference between the tip 32 and the field emission extraction electrode 66. Alternatively, an optional electrical lead 69 may be connected to a voltage supply (not shown) when the optional coating of material 48 is to be utilized as the field emission extraction electrode.

The relatively larger single walled carbon nanotubes in FIGS. 2 and 3 may be quite long compared to their diameter, e.g. on the order of a micron or more; in general, such nanotubes have aspect ratios of at least about 1:10 to 1:1000. The material properties (such as toughness and springiness of such nanotubes) may be adapted to allow the nanotubes to optionally be subjected to mechanical bending involving various high frequency resonant motion patterns, in the kilohertz through megahertz range, depending on specific geometry for purposes of directing, diverting, modulating, or scanning the emergent electron beam.

There are several forms of carbon nanotubes. In general, the most commonly studied forms of carbon nanotubes have physical properties such that they conduct electricity better than copper, they have a tensile strengths over 100 times that of steel, they become superconductors when cooled to extremely low temperatures, and they are exceptionally tough and resilient when subjected to mechanical bending.

The electron transparent structures illustrated in the Figures can be formed by the carbon nanotube end caps 46 shown in FIGS. 2 and 3. Alternatively, or additionally, these electron transparent structures may be replaced, in part or in whole, by mechanically attaching some other ultra thin film of suitably electron transparent material to the end of an uncapped carbon nanotube.

The micro-enclosed point source electron beam generators 10 of FIG. 1 and 32 of FIGS. 2 and 3 may be mechanically scanned near the target to be imaged or incorporated into the tip of an atomic force microscope for the purpose of very high resolution electron microscopy and spectroscopy; or such point source electron beam generators 10 of FIG. 1 and 32 of FIGS. 2 and 3 can be incorporated into an electron beam micro-column, such as described in "Fabrication of electron-beam microcolumn aligned by scanning tunneling microscope", Jeong-Young Park, et al, Journal of Vacuum Science and Technology A, Volume 15, Number 3, May/Jun 1997, 1499–1502.

Figure 4:
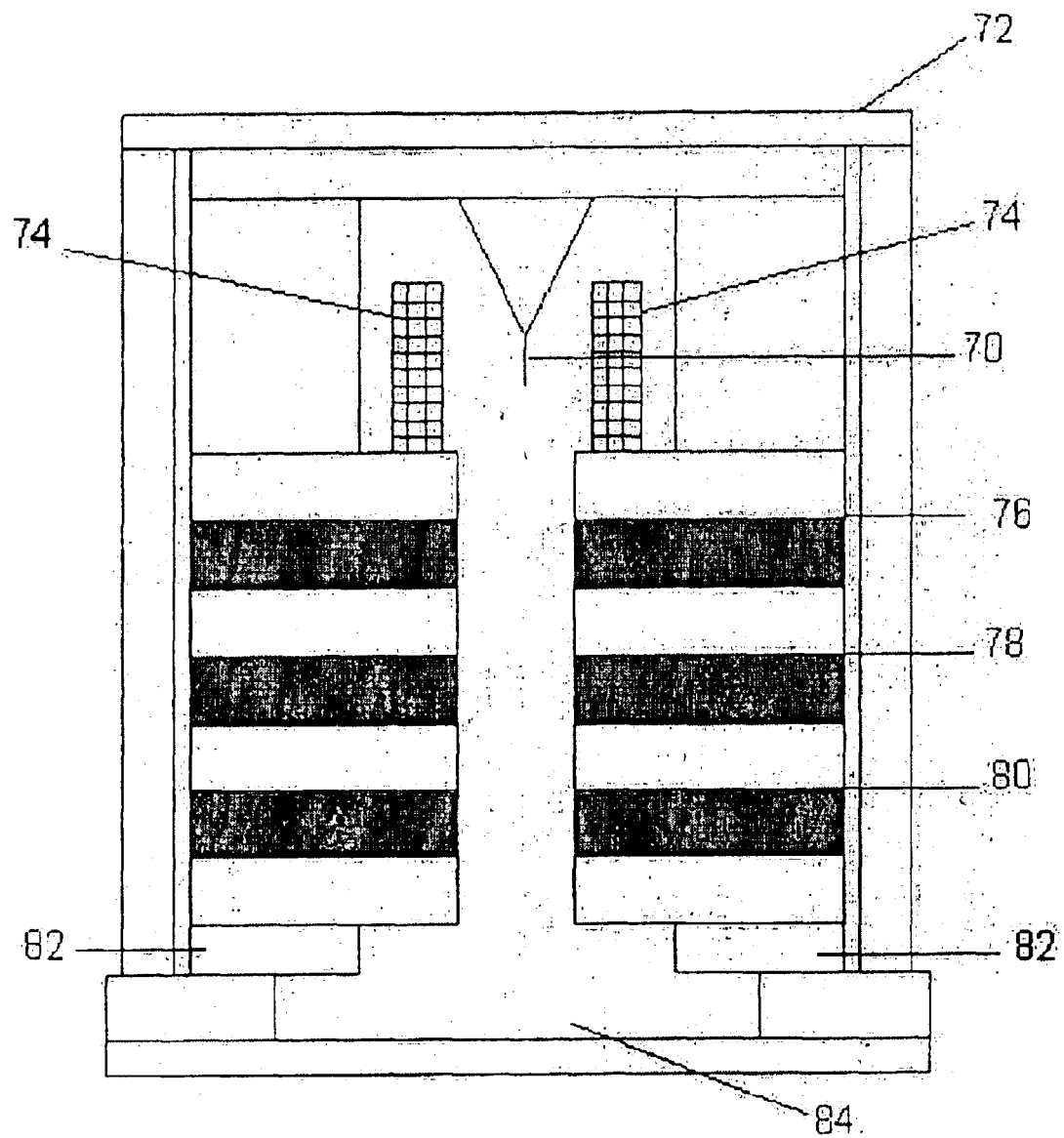
FIG. 4 is a schematic representation of a miniature scanning electron microscope using an enclosed point source electron beam generator.

FIG. 4 illustrates the use of a micro-enclosed point source of electrons 70, (which may consist of any of the systems shown in FIGS. 1, 2, and 3) to substantially improve on other devices, such as, e.g., the device disclosed in Thomas George's "Miniature Electron Microscopes Without Vacuum Pumps", NASA Technical Brief, Vol. 22, No. 8. (JPL NEW TECHNOLOGY REPORT NPO-20335). A low-to-medium vacuum enclosure 72 contains the whole system; in general, the pressure within enclosure 72 is from about $10^{-3}$ to $10^{-6}$ Torr. An optional superconducting cylinder 74 can be used for narrowing the conical emerging electron beam. An optional beam extraction electrode and/or beam acceleration or deceleration electrodes 76 may be used. Electrode pair 78 and electrode 80 are used for scan deflection and focus. Backscattered electron detectors 82 are placed above the observation and manipulation stage 84. Secondary and backscattered electrons may be detected either by a micro channel plate, or a channeltron, or by other conventional means.

Figure 5:
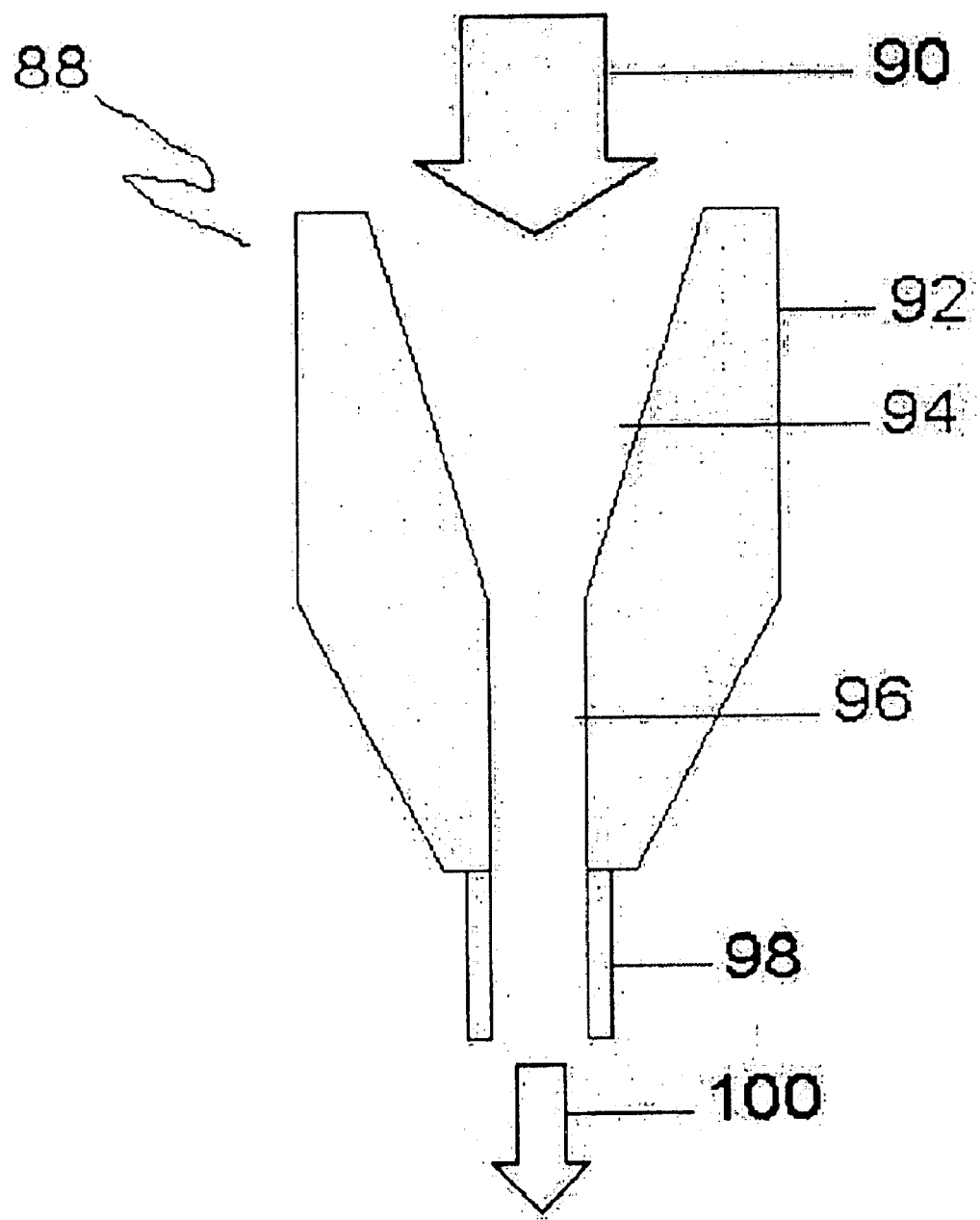
FIG. 5 is a schematic representation of an electron beam focusing coupler for a superconducting nano-channel.

The use of superconducting channels for manipulating electron beams has been described in "High Tc bulk superconductor wigglers", Hidenori Matsuzawa, et al, Applied Physics Letters, Volume 59, Number 2, Jul. 8, 1991, 141–142. FIG. 5 shows how a relatively large (in the range of approximately 0.1 to 100 micron diameter) beam of electrons or positive ions 90 may be narrowed into a beam 100 by means of a superconducting channel assembly 88. Beam 90 passes through superconducting material 92 with a converging funnel channel 94 to a channel 96 of dimensions in the range of approximately 1 to 100 nanometer diameter, and through a connected single walled superconducting carbon nanotube 98. The superconducting structure 92 may optionally be split in planes perpendicular to the funnel axis into several mutually insulating segments that are mutually electrified so as to facilitate the attraction of electrons into each successive segment.

Figure 6:
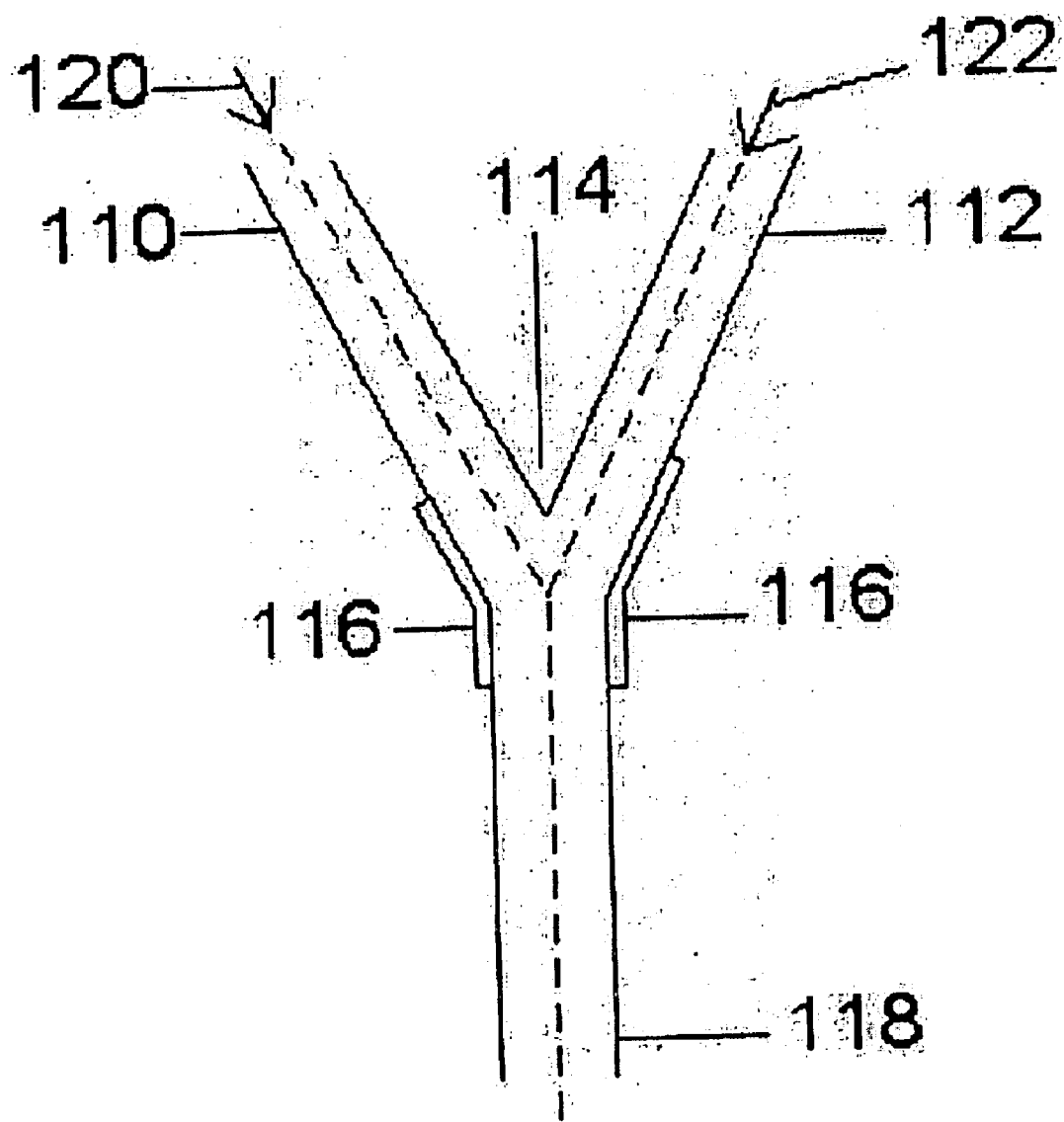
FIG. 6 is a schematic representation of a superconducting nano-channel Y junction.

FIG. 6 illustrates the use of superconducting carbon nanotubes 110, 112 in the range of about 0.3 to 100 nanometers in diameter constructed into a Y-junction 114. Because superconductivity is likely substantially reduced in the junction region itself, this region would normally be externally coated with a thin film of superconducting material 116. The more general use of high temperature superconductors for such coatings and the coating of all channels removes the requirement that the carbon nanotubes be superconducting or be used at the temperature at which they are superconducting. This system can be used to couple an electron beam 120 with an ion beam 122 or with another source of electrons at a different energy level, from inlets 110, 112 into the Y-junction 114 and to the single coaxial outlet 118. One of several means of using such a system is to use the electron beam for target illumination and positioning purposes, and using the ion beam for transient milling or ion deposition purposes.

Figure 7:
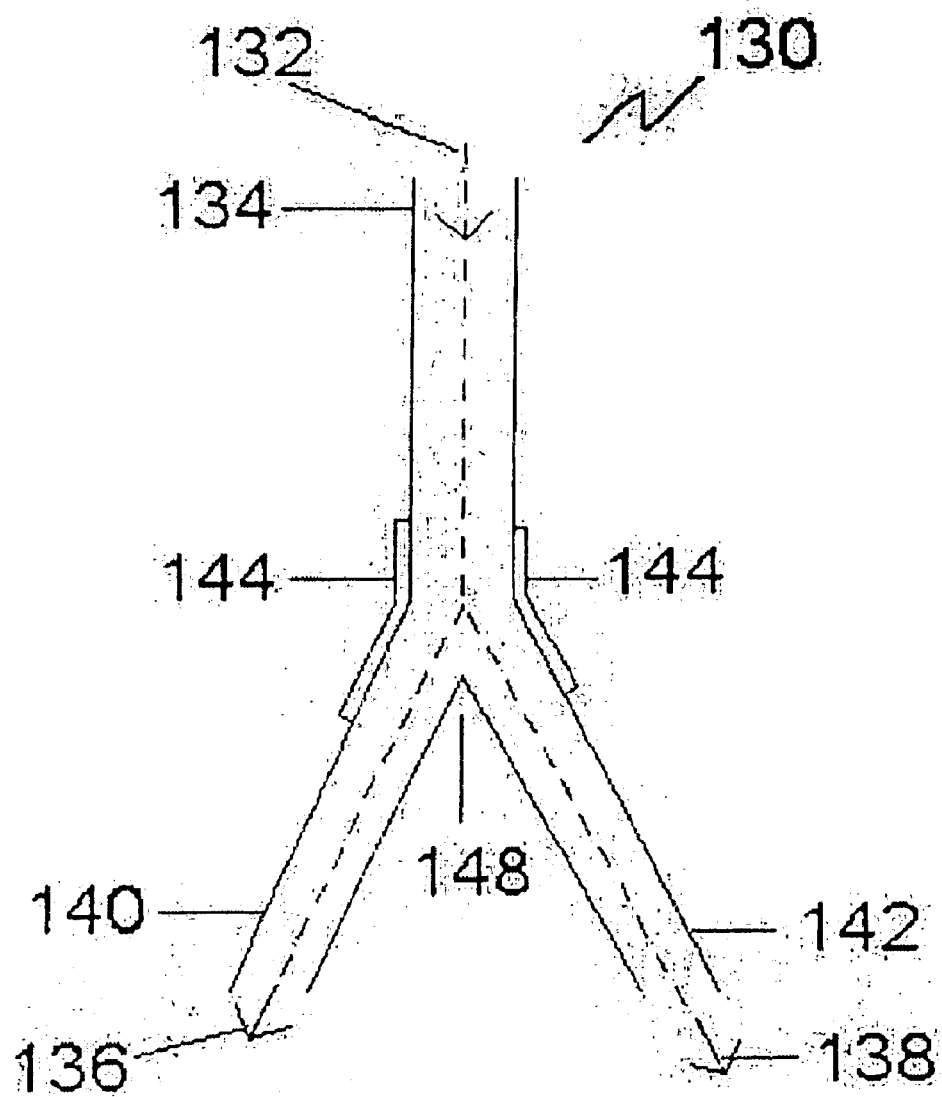
FIG. 7 is a schematic representation of a superconducting nano-channel Y junction.

Alternatively, the Y-junction assembly 130 shown in FIG. 7 can be used to split an electron beam 132 entering inlet 134 into 2 beams 136, 138 exiting at outlets 140, 142. Additional thin film coating 144 of a superconducting material may optionally be employed to enhance the superconducting property at the junction 148. Such junctions need not be symmetric in branching angles or in terms of nanotube diameters. Multiple such splitting and merging junctions may be combined in practice, and may be structured so as to implement nano-scale electron beam analogs of fluidic technology, including feedback loops. Modulation mechanisms may be provided by external pulsed magnetic fields above the local superconducting shielding level, induction of trapped magnetic fields inside and along the axis of nano-channel loops, locally induced transient thermal excursions above the superconducting threshold temperature, mechanical bending, and the use of electrically insulated superconducting channel segments at differing potentials. These can be used in vacuum electronic device systems that dispense with individual solid state cathodes and individual solid state anodes. Such systems can also be realized without using carbon nanotubes, by exploiting the fabrication techniques that are used for micro-electro-mechanical systems. Such device systems can implement analog and digital types of transducer, signal processing, and computing functions. The highly modulated electron beam output of such systems can be used for subsequently miniaturized electron microscopy implementation, and for corollary use in spatially resolved electrochemistry processes.

Figure 8:
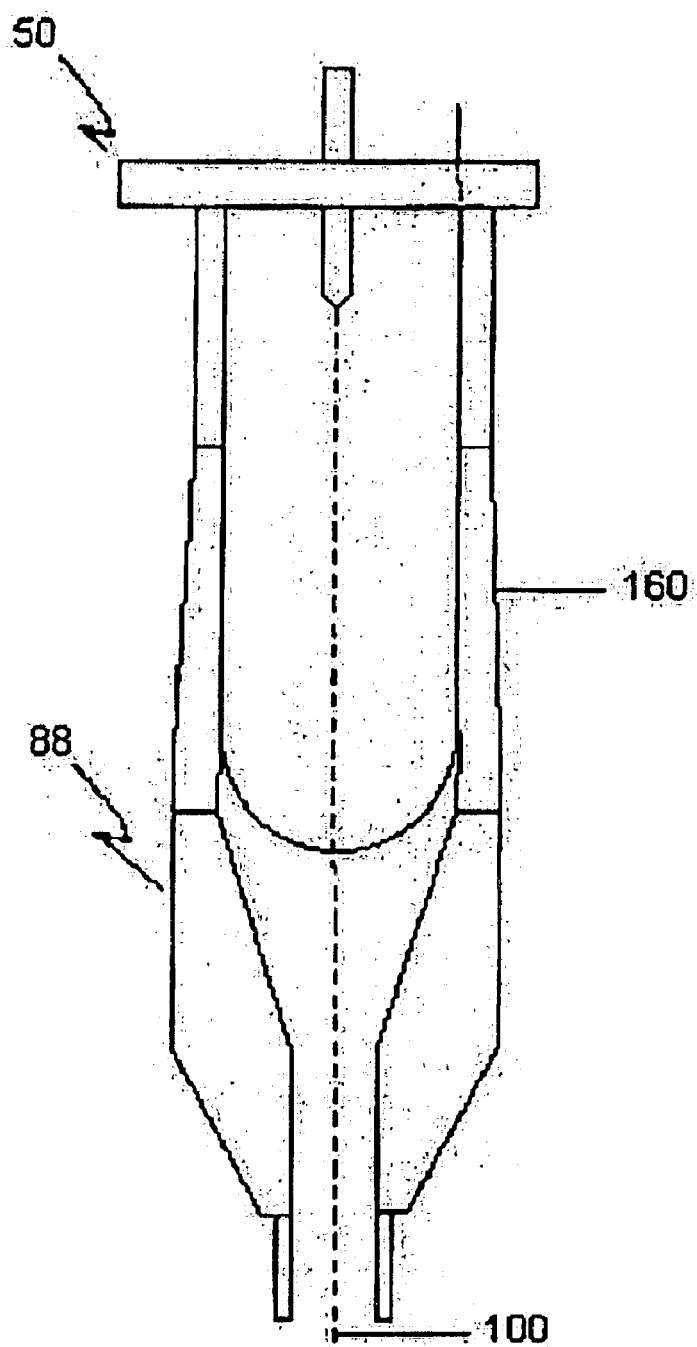
FIG. 8 is a schematic representation of a point source electron beam generator coupled to an electron beam focusing superconducting nano-channel.

FIG. 8 illustrates one preferred use of the electron beam emitter assembly 50 of FIG. 2 together with the superconducting channel assemble 88 of FIG. 5. A material 160 is used to attach assembly 50 to the assembly 88. In one embodiment, material 160 is a non-conducting material, e.g. Nylon-6, Nylon-66, Teflon or the like, and electrically isolates assembly 50 from assembly 88. In another embodiment, material 160 is a superconducting material.

The ability to generate, guide and manipulate electron beams or other charged particle is an essential feature of microscopy devices, such as e.g., Scanning Tunneling Microscopes (STM) and Atomic Force Microscopes (AFM). The superconducting nano-channel structures of this invention, comprising carbon-based nanotubes, may be used with microscopy probes. They may also operate with a miniature ultra-high vacuum enclosure with an electron-transparent widow.

Free standing flexible superconducting nanometer scale tubes and fixed superconducting nanometer scale channels formed on supporting substrates, manufactured by means well known to those skilled in the art of micro-lithography and related micro-fabrication techniques, may be further used for conveying coherent electron beams with energies corresponding to wavelengths of a similar order of magnitude (e.g. a few electron volts) and provides a nanometer scale electron beam analog of micron scale fiber optical systems.

Figure 9:
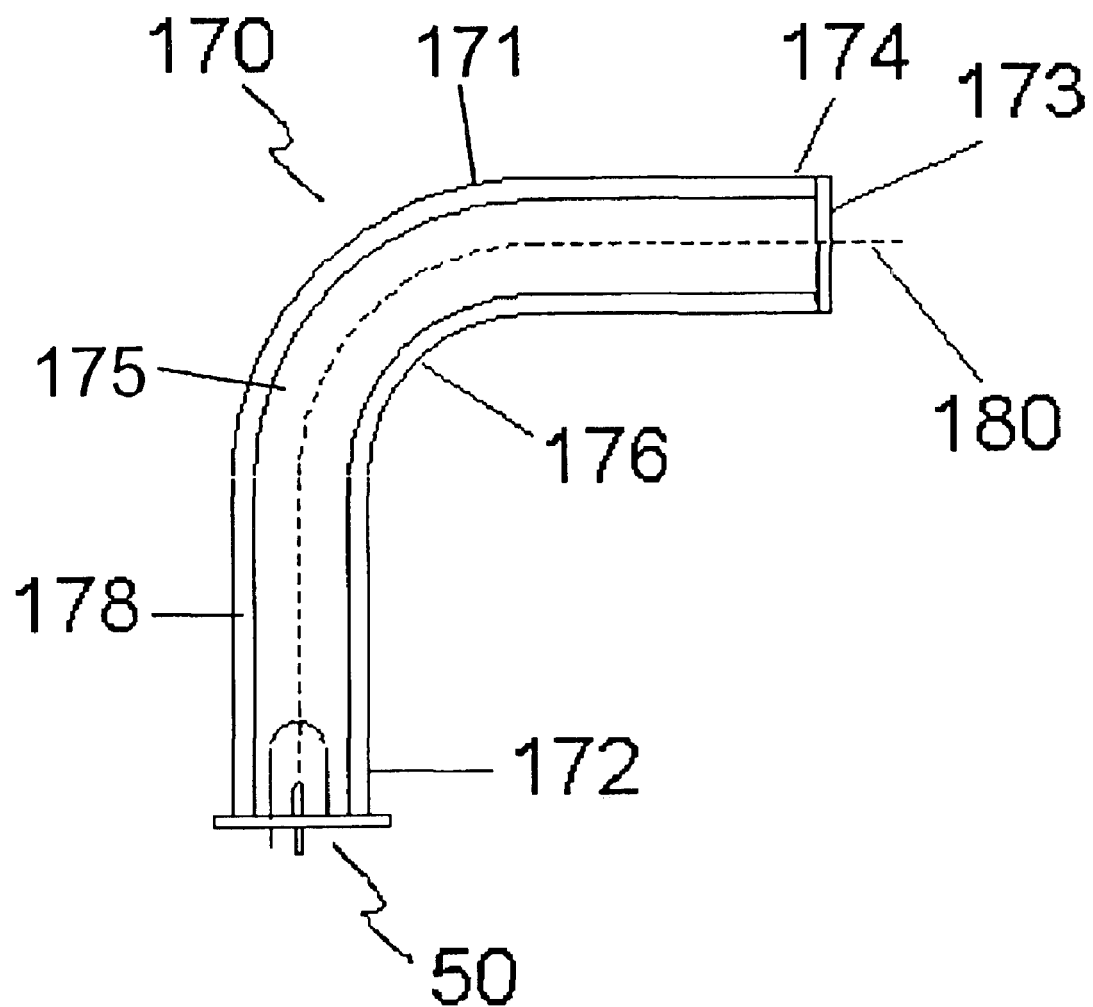
FIG. 9 is a schematic representation of one embodiment of a device for guiding charged particle beams comprising a superconducting nano-channel.

FIG. 9 is a schematic representation of one embodiment of a device for guiding charged particle beams comprising a superconducting nano-channel. Referring to FIG. 9, device 170 comprises a superconducting channel 171 consisting essentially of a superconducting material 178 in the form of a tube, for guiding electron beam or other charged particle beam 180. In the embodiment depicted in FIG. 9, beam 180 passes through an approximately 90 degree bend 176 in the channel 171 and exits at the channel distal end 174. In other embodiments, bend 176 may be constructed with a structure having an arc of other than 90 degrees. Bend 176 is preferably greater than zero degrees, and as much as 180 degrees in an embodiment wherein the direction of the particle beam 180 is to be substantially reversed.

In a further embodiment, charged particle beam guiding device 170 is an apparatus for generating and guiding a charged particle beam. Referring again to FIG. 9, apparatus 170 comprises a point source particle beam generator coupled to a superconducting nano-channel, the end thereof being sealed with an electron beam transparent membrane. FIG. 9 illustrates a preferred embodiment in which electron beam emitter assembly 50 is coupled to superconducting channel 171 for conveyance of coherent electron beam 180. At the proximal end 172 of channel 171 is attached electron source 50. An electron transparent window 173 is sealed to channel end 174 to form an ultra-high vacuum region 175 through which electron beam 180 travels. Because of the nano-scale dimensions of superconducting channel 171, ultra-high vacuum conditions may be achieved within region 175.

It will be apparent that any of the enclosed point source electron beam generators previously described and shown in FIGS. 1, 2, or 3 will be suitable for electron source 50. It will be further apparent that electron transparent membrane or window 173 may be either substantially planar, or a semi-spherical cap, and of the materials previously described in this specification and shown in FIGS. 1, 2, and 3.

Figure 10A:
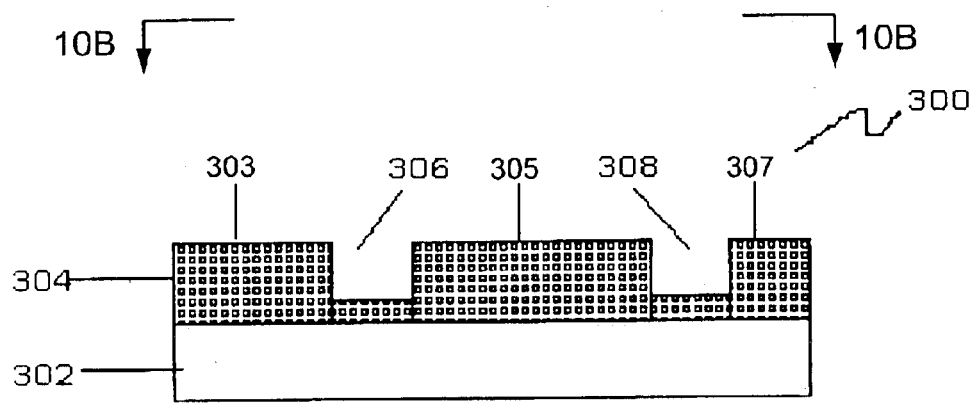
FIG. 10A is a schematic representation of a side view of a superconducting nano-channel network.
Figure 10B:
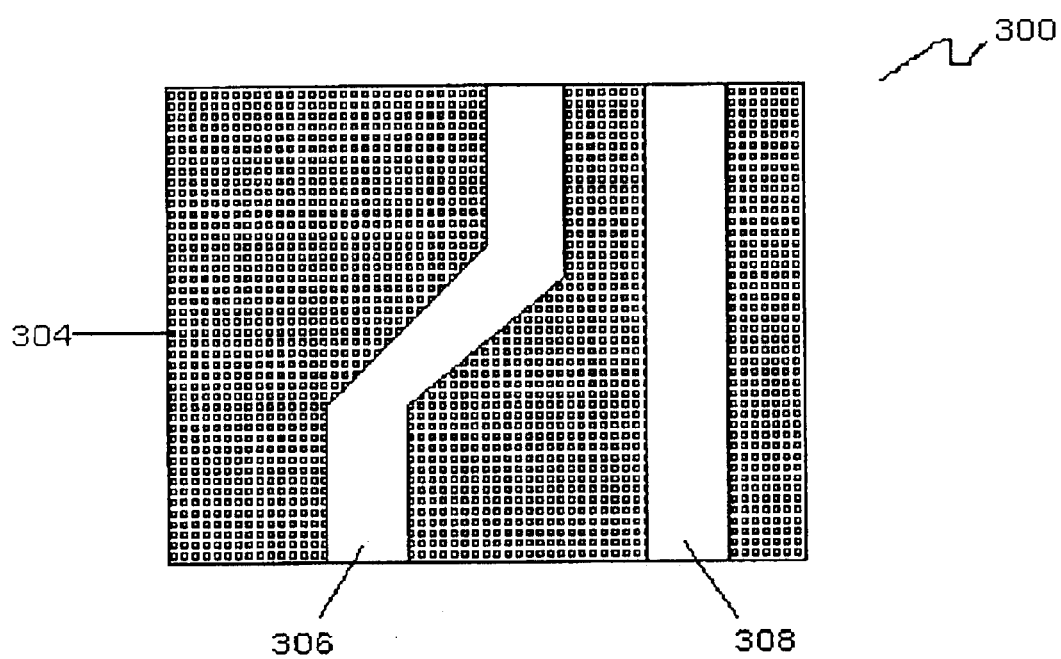
FIG. 10B is a top view of the representation of FIG. 10A taken along line 10B—10B of FIG. 10A.

FIG. 10A is a schematic representation of a side view of a superconducting nano-channel network, and FIG. 10B is a top view of the representation of FIG. 10A taken along line 10B—10B of FIG. 10A. FIGS. 10A and 10B illustrate a preferred embodiment in which 2-D, "2.5-D", and 3-D superconducting nano-channels may be fabricated on a substrate using lithographic or stereo-lithographic means.

Referring to FIGS. 10A and 10B, assembly 300 comprises substrate 302 onto which superconducting material 304 is deposited by means known in the art. Superconducting nano-channels 306 and 308 may be formed using lithography or stereo-lithography, or other suitable micro-fabrication means, wherein areas 303, 305, and 307 of material 304 have edges substantially parallel to each other, thereby forming channels 306 and 308. In one embodiment, additional layers of superconducting material (not shown) may be deposited on top of superconducting material 304 to completely enclose channels 306 and 308, and to provide additional channels (not shown), thus forming a complex network of superconducting channels. Electron beams or other charged particles may be guided and manipulated through the network of superconducting channels taking advantage of the Meissner effect of superconductors (repulsion forces). Layers of insulating material (not shown) may be deposited so that the complex network of superconducting nano-channels may be segmented into sections held at different electrical potentials by one or more power sources (not shown). Superconducting material 304 may comprise C60 hybrids or boron nitride. Superconducting nano-channel networks may be combined with conventional integrated circuit technology to fabricate integrated (nano and pico-beam) vacuum nano-electronic devices (both digital and analog). These devices may be used to generate and modulate nano and pico-electron beams for high-resolution imaging, or for gathering and processing information obtained from detectors and transducers.

It will be apparent that although a two dimensional embodiment is depicted in FIGS. 10A and 10B, three dimensional embodiments may be readily fabricated wherein the substrate 302 has a three dimensional topography.

Figure 11A:
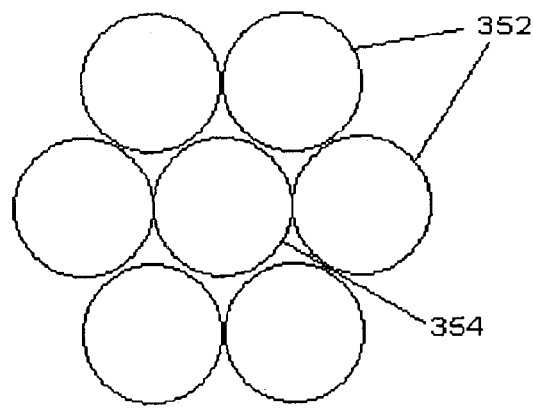
FIGS. 11A, 11B, and 11C are schematic representations of embodiments of superconducting nano-channels having nano-scale superconducting rods.
Figure 11B:
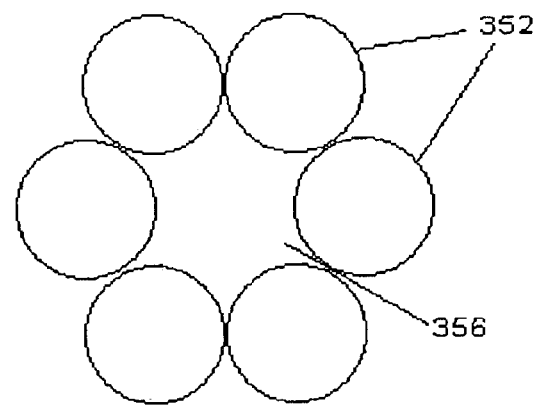
Figure 11C:
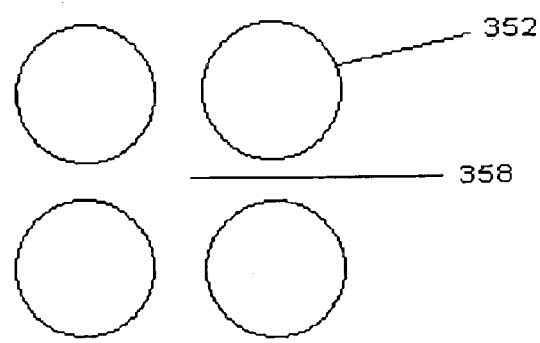

FIGS. 11A, 11B, and 11C are schematic representations of embodiments of superconducting nano-channels having nano-scale superconducting rods. FIGS. 11A, 11B, and 11C illustrate preferred embodiments in which a superconducting nano-channel suitable for guiding and manipulating nano-electron beams and other charged particles may be formed by geometrically arranging nano-scale superconducting rods or wires around a central region.

Referring to FIG. 11A, and in the embodiment depicted therein, rods 352 are provided with a substantially circular cross section. Rods 352 are arranged in physical contact with one another, around center rod 354. Referring to FIG. 11B, central rod 354 is removed to form a central superconducting nano-channel 356 bounded by superconducting rods 352. Electron beams or other charged particles may flow through channel 356.

Referring to FIG. 11C, in an alternate embodiment comprising four rods 352, superconducting rods 352 arranged around central superconducting nano-channel 358, through which electron beams or other charged particles may flow. In the embodiment depicted in FIG. 11C, superconducting rods 352 are not in physical contact with one another. It is to be understood, that superconducting rods 352 may have cross sections other than a circular one. It is also to be understood that superconducting rods 352 may not be continuously straight along their length, they may or may not be solid in cross section, and may or may not be held at the same electrical potential by one or more power source (not shown) unless they are in electrical contact. Superconducting rods 352 may be coated with conductive material (not shown). Any suitable scaffold or similar device, many of which are known to those skilled in the art, may be used to hold superconducting rods 352 together.

Figure 12:
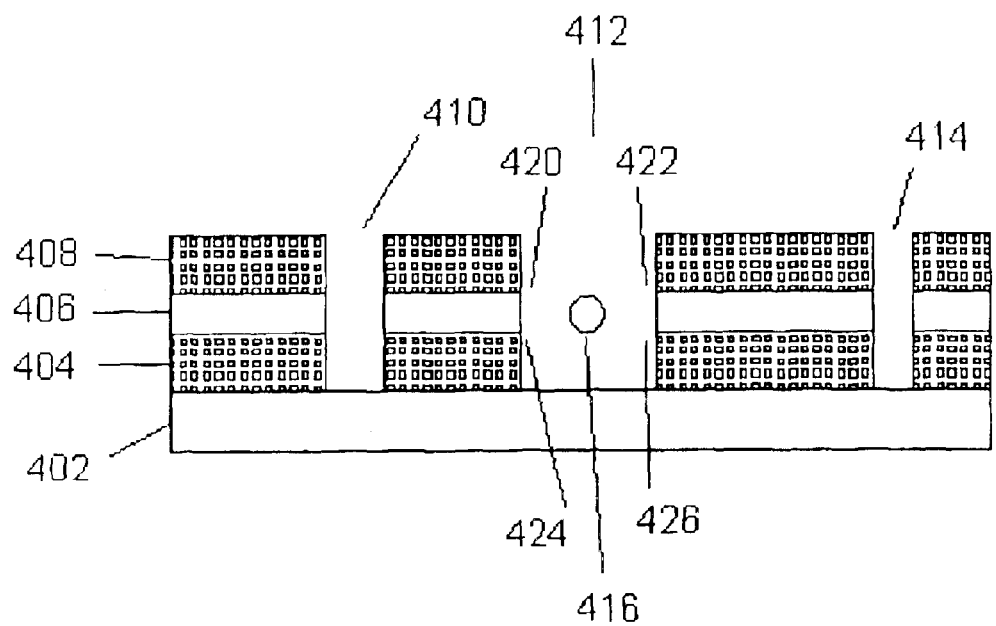
FIG. 12 is a schematic representation of a superconducting nano-channel having multiple layers.

FIG. 12 is a schematic representation of a superconducting nano-channel having multiple layers. FIG. 12 illustrates a preferred embodiment in which a layer of superconducting material 404 is deposited on substrate 402. Referring to FIG. 12, a layer of non-conducting material 406 is deposited on top of superconducting layer 404. Another layer of superconducting material 408 is then deposited on top of non-conducting layer 406. Superconducting channels 410, 412, and 414 may be formed using conventional lithographic techniques. The relative degree of confinement of each superconducting nano-channels 410, 412, and 414 may be geometrically modulated to suit any particular application. For example, superconducting nano-channels 410 and 414 would be more strongly confining than superconducting nano-channel 412, due to the greater relative enclosure of superconducting material. On the other hand, charged particles 416 traveling through superconducting channel 412 will experience Meissner effect repulsion originating from the four quadrants 420, 422, 424, and 426. The structures described in this and other embodiments of this invention may be combined with conventional integrated circuits and micro electro-mechanical fabrication techniques to produce, but not limited to, imaging and detecting devices.

Figure 13A:
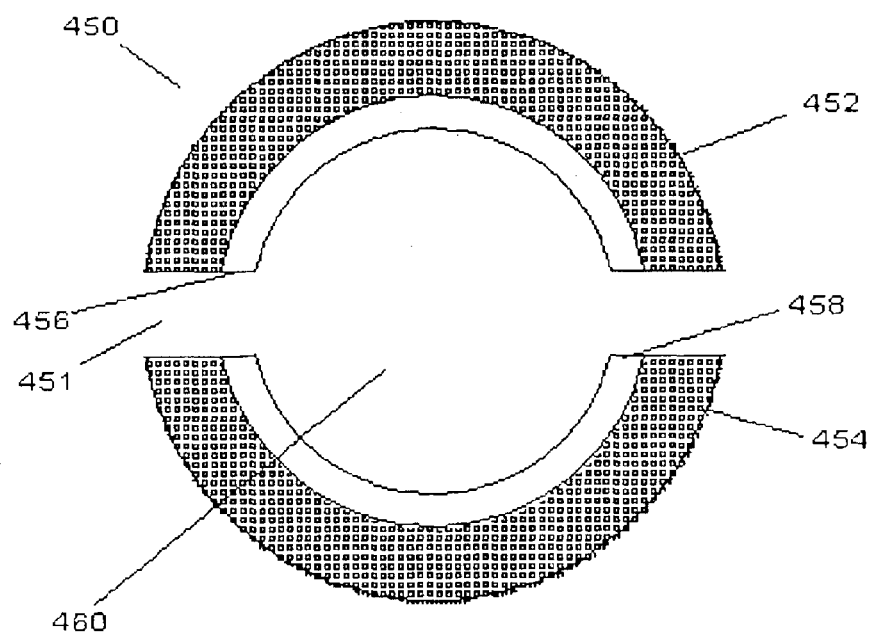
FIGS. 13A and 13B are schematic representations of embodiments of a superconducting nano-channel split in the axial direction.
Figure 13B:
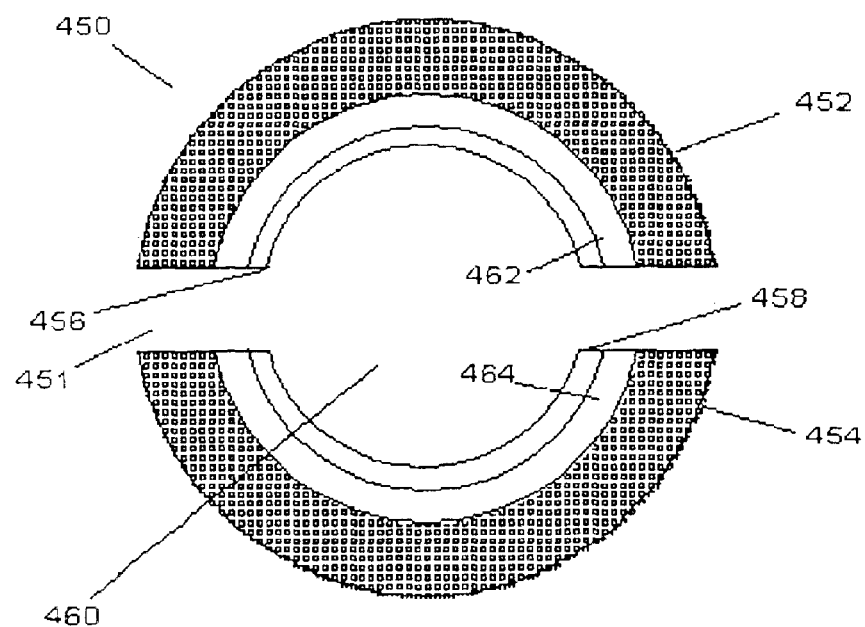

FIGS. 13A and 13B are schematic representations of embodiments of a superconducting nano-channel split in the axial direction, i.e. parallel to the central axis of the nano-channel. FIGS. 13A and 13B illustrate a preferred embodiment in which the superconducting nano-channel is a superconducting nano-cylinder. Referring to FIG. 13A, superconducting nano-cylinder 450 is axially split into two half-cylinders 452 and 454 separated by a small gap 451. A layer of conductive material 456 and 458 may be applied to the inner surfaces of half-cylinders 452 and 454.

Referring to FIG. 13B, a layer of insulating material 462 and 464 separates the inner surface of half-cylinders 452 and 454 and the layer of conductive material 456 and 458. A very small voltage provided by a power source (not shown) may be applied across conductive material 456 and 458. This arrangement would force charged particles traveling through superconducting channel 460 to orient with the electric field within superconducting channel 460 if the charge distribution of said traveling charged particles is in the least asymmetric.

In another embodiment (not shown) superconducting nano-cylinder 450 may be twisted into other shapes, including a double helical slit, so as to impart a torque on particles traveling through superconducting channel 460. Alternatively, superconducting nano-cylinder 450 could be split in several places, creating a plurality of superconducting segments that could be driven by a polyphase AC signal to impart a torque on particles traveling through superconducting channel 460, but in a readily variable and electronically controlled fashion. An axial cylindrical split into ⅓ and ⅔ radial segments (with an optional helical twist) would "reflect back" a non-uniform repulsive magnetic field.

Figure 14:
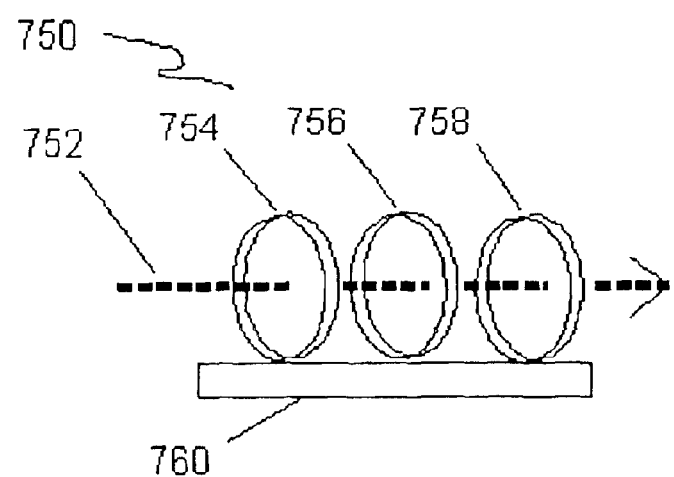
FIG. 14 is a schematic representation of a superconducting nano-channel connected to a support system.

FIG. 14 is a schematic representation of a superconducting nano-channel connected to a support system. Referring to FIG. 14, there is depicted assembly 750, in which superconducting nano-wires are used to make superconducting loops 754, 756, and 758, which are connected to a support system 760. Superconducting loops 754, 756, and 758 constitute an approximation to a whole superconducting tube.

Dividing a superconducting tube into a plurality of superconducting loops offers the same properties of a whole tube while providing additional means for shaping and modulating the charged particle beam. Charged particles 752 traveling through superconducting loops 754, 756, and 758 will experience Meissner effect (repulsion forces). Many other (not shown) wire-like and/or ribbon-like shapes, e.g., ellipses, semicircles, baseball seam curves, U-shaped loops, etc., may be configured as superconducting nano-channels approximations through which charged particles may travel. These shapes may additionally be electrically charged or magnetized (by running electrical currents through them), thereby affording a multiplicity of characteristic particle optical effects. Depending on the relative size and position of such shape superconducting elements relative to charged nano or picobeam trajectories, such shapes may be subject to electrostatic charging, which would alter their particle optical effects. Likewise, depending on the type of support structure used, such shapes may have predetermined discharge rates, and may be cross-coupled to other shapes. Furthermore, the anode currents of electrically split anodes in the path of deflectable charged picobeams may be used to differentially drive various electric or magnetic superconducting shapes, thus influencing the trajectory of the same or other charged nano or picobeams. The use of flexible shapes or flexible mounts adds another dimension of possibilities, both for simple deflection and for multiple mechanical resonance modes, especially since even very small motions can have a geometrically magnified leverage effect on charged nano or picobeams, or an exponentially magnified leverage effect on tunnel currents across small gaps.

Figure 15A:
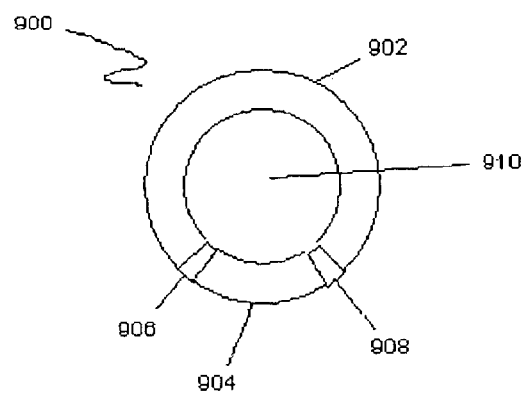
FIGS. 15A, 15B, and 15C are schematic representations of embodiments of superconducting nano-channels split into unequal portions.
Figure 15B:
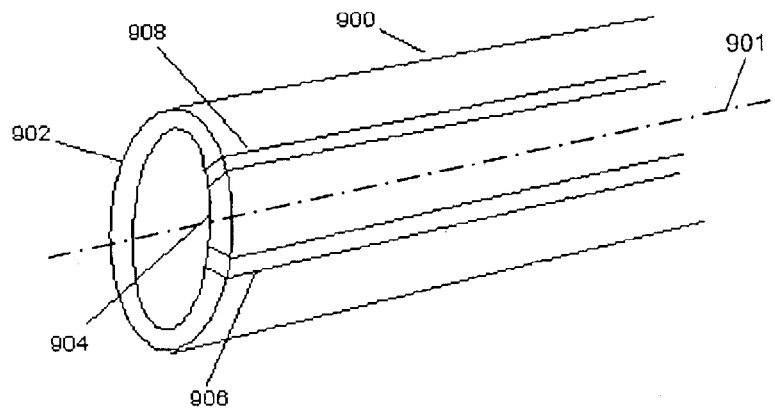
Figure 15C:
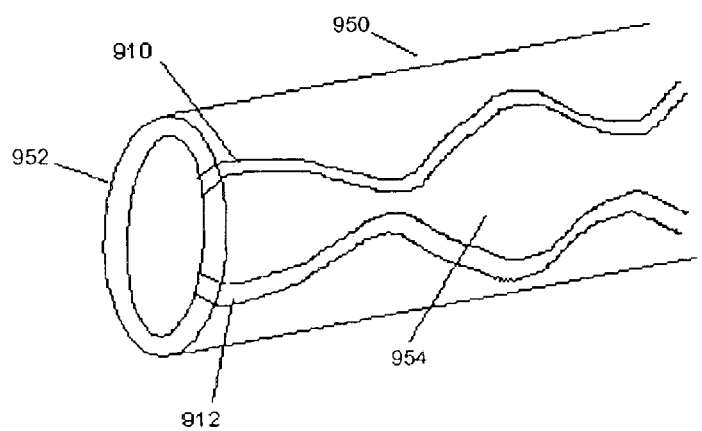

FIGS. 15A, 15B, and 15C are schematic representations of embodiments of superconducting nano-channels split into unequal portions. FIGS. 15A and 15B illustrate a preferred embodiments in which a superconducting cylinder 900, e.g., a superconducting nano-tube which is split into unequal portions along its length by straight split lines 906 and 908, which are parallel to central axis 901 of cylinder 900. FIG. 15B is a perspective view of the embodiment depicted in FIG. 15A. Referring to FIGS. 15A and 15B, superconducting cylinder 900 is split into a major superconducting segment 902 and a minor superconducting segment 904, which have different arc displacements but are of the same radius of curvature. Non-superconducting material in gaps 906 and 908 may be used to hold superconducting segments 902 and 904 together.

FIG. 15C illustrates another embodiments in which a superconducting cylinder 950 is split into a major superconducting segment 902 and a minor superconducting segment 904 by non-straight split lines 910 and 912. Superconducting segment 952 and a minor superconducting segment 954 have different sizes and different shapes. Non-superconducting material may be used to hold superconducting segments 952 and 954 together as described previously.

FIGS. 16A–16D are schematic representations of embodiments of merging superconducting nano-channels. In like manner, superconducting nano-channel approximations as described in the embodiment depicted in FIG. 14 may also be merged together. Merged superconducting nano-channels may be used to mix injected charged particles. They may also be used as transport assemblies for charged particles, or to modulate one charged particle beam with another. They may also be used to dynamically switch the trajectory of charged particles from one nano-channel to another.

Figure 16A:
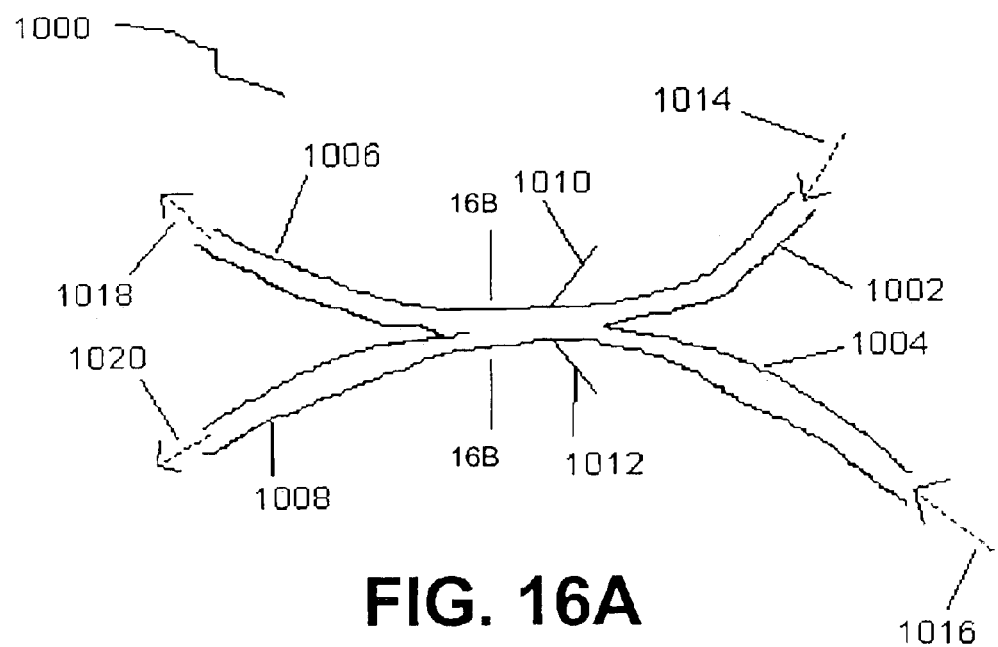
FIGS. 16A–16D are schematic representations of embodiments of merging superconducting nano-channels.

Referring to FIG. 16A, superconducting assembly 1000 is shown in which superconducting nano-channels 1002 and 1004, into which charged particle beams 1014 and 1016 are injected and mixed, are first merged together and then separated, forming exit superconducting nano-channels 1006 and 1008, from which charged particle beams 1018 and 1020 emerge. Electrical leads 1010 and 1012 may be used to provide electrical power supplied by a power source (not shown).

Figure 16B:
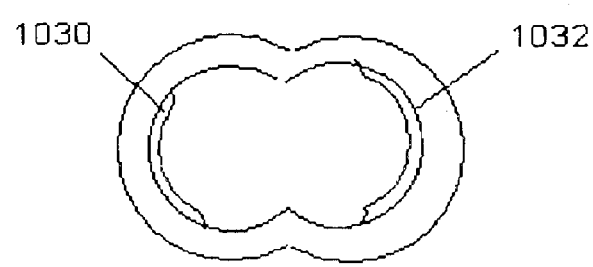

FIG. 16B shows a sectional view of the merged superconducting nano-channels through line 16B—16B of FIG. 16A. In the embodiment depicted in FIG. 16B, electrical conductors 1030 and 1032 located on the inner surface of superconducting assembly 1000 are provided. Referring to FIGS. 16A and 16B, by applying a potential difference to electrically isolated electrical conductors 1030 and 1032, charged particle beams 1014 and/or 1016 may have their exit trajectories switched between superconducting nano-channels 1006 and 1008 to emerge as charged particle beams 1018 or 1020. The walls of superconducting assembly 1000 as shown in FIG. 16A may be partitioned into nearly contiguous but electrically isolated segments, thus negating to need to have separate electrical conductors 1030 and 1032.

Figure 16C:
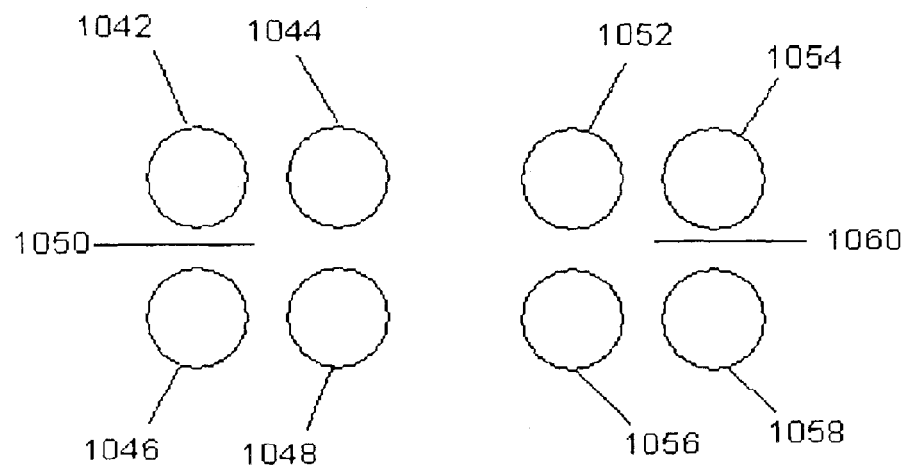

FIG. 16C illustrates a preferred embodiment in which superconducting rods made of superconducting nano-wires are used to form an approximation to a superconducting nanotube, as previously described in the embodiments shown in FIGS. 11A–11C. Referring to FIG. 16C, superconducting nano-channel 1002 (see FIG. 16A) is approximated by superconducting rods 1042, 1044, 1046, and 1048, to define superconducting nano-channel 1050. Likewise, superconducting nano-channel 1004 (see FIG. 16A) is approximated by superconducting nano-rods 1052, 1054, 1056, and 1058 to define superconducting nano-channel 1060. Electron beams or other charged particles traveling through superconducting nano-channels 1050 and 1060 may be guided and manipulated, taking advantage of the Meissner effect (repulsion forces).

Figure 16D:
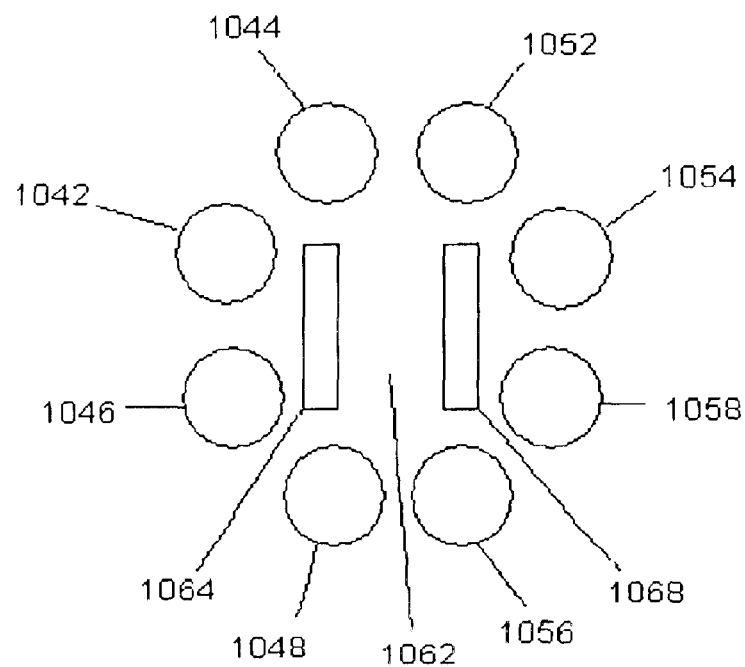

Referring to FIG. 16D, cross sectional view of a superconducting nano-channel created by the merging of superconducting nano-channels 1002 and 1004 at a plane defined by line 16B—16B (as shown in FIG. 16A) is replaced by the approximation defined by superconducting nano-channel 1062, which is created by superconducting rods 1042, 1044, 1046, 1048, 1052, 1054, 1056, and 1058, which in turn are positioned at the corner points of an octagon. An electrical voltage provided by a power source (not shown) may be applied to electrical conductors 1064 and 1068 to guide and manipulate electron beams or other charged particles traveling through superconducting nano-channel 1062. Superconducting nano-channel 1062 thus becomes a switching region where electron beams or other charged particles may be guided to the desired exit channels as described in the embodiment shown in FIG. 16A.

Figure 17:
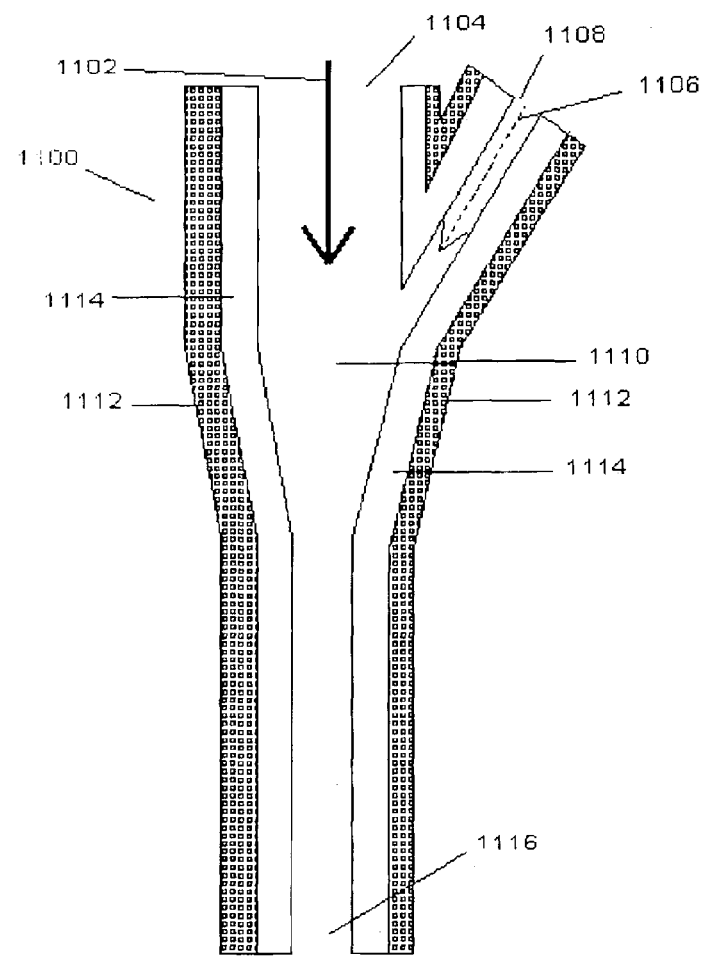
FIG. 17 is a schematic representation of a superconducting nano-channel Y-junction.

FIG. 17 is a schematic representation of a superconducting nano-channel Y-junction. FIG. 17 illustrates a preferred embodiment in which superconducting glass capillaries may be used to guide and manipulate electron beams and other charge particles. Superconducting glass capillaries, with exit ports as small as about 10 nanometers, have an advantageously amorphous and anatomically smooth surface. They may be used for merging, for example, x-rays (both hard x-rays and soft x-rays) and electron beams (both nano and pico beams) or other charged particles. Superconducting glass capillaries may be able to produce geometric beam energy concentration gains on the order of 1000 or more.

Referring to FIG. 17, there is shown a Y-shaped glass capillary 1100 having its inner surface coated with a glass layer 1114, and having its outer surface coated with a layer of superconducting material 1112. Superconducting glass capillary 1100 comprises entry ports 1104 and 1108, and a very narrow exit port 1116. A controllably, intermittent x-ray beam 1102 is introduced into port 1104 and is guided by glass layer 1114, while a controllably, intermittent electron beam or other charged particle beam 1106 is introduced into port 1108 by a side branch coupler (not shown) and is guided by superconducting material layer 1112. Charged particle beam 1106 is introduced at a suitable angle relative to x-ray beam 1102 in order to minimally impact and minimally intercept the x-ray beam 1102. After reaching the intersection area 1110 (i.e. shared space), both beams 1102 and 1106 begin to narrow their spread, before exiting the superconducting glass capillary 1100 through narrow exit port 1116. Both beams 1102 and 1106 are controllably turned ON and OFF by suitable means (not shown) to select which beam (mode) is in operation.

These hybrid superconducting nano-channels, so described because of their ability to guide and manipulate a plurality of beams, may be used for multi-mode imaging, microanalysis, lithography and stereolitography. An application of how this mode switching may be used to perform two distinct functions almost simultaneously will be described as follows: in a first mode, charged particles might be guided and manipulated for imaging and identifying the topography or other feature of a substrate for subsequent x-ray irradiation by a second mode. In another application, electronic beams or other charged particle beams may be modulated over the shared space with intensely concentrated x-rays (or vice versa, with suitable adjustments of electron energy and nano-channel diameter). Additional interactions involving other types of charged particles or nano-particle beams, including transient electron states and ionization is to be considered within the scope of this invention.

Figure 18:
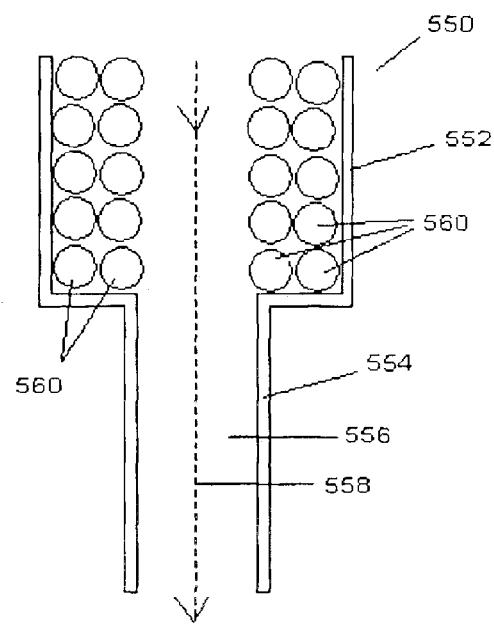
FIG. 18 is a schematic representation of a superconducting nano-channel with internal superconducting wires.

FIG. 18 is a schematic representation of a superconducting nano-channel with internal superconducting wires. FIG. 18 illustrates a preferred embodiment in which superconducting nano-channels have different diameters at their respective ends. In the case of unidirectional propagation, the beam input end has a larger diameter than the beam exit end. The larger diameter allows the superconducting nano-channels to internally accommodate a plurality of superconducting wires defining coaxial structures, which may be arranged in a straight, helical, or other suitable configurations. An electrical potential provided by a power source (not shown) may be applied to the coaxial structures to modulate the axial and radial velocity components of electron beams or other charged particles traveling through the superconducting nano-channel.

Referring to FIG. 18, superconducting nano-channel 550 is shown having a beam input end 552 and a beam exit end 554. The diameter of beam input end 552 is larger than the diameter of beam output end 554. Beam input end 552 accommodates a coaxial structure comprising superconducting nano-wires 560. An electrical potential provided by an electrical source (not shown) and applied to superconducting nano-wires 560 may be used to modulate the axial and radial velocity components of electron beam or other charged particle beam 558 traveling through central channel 556.

Figure 19:
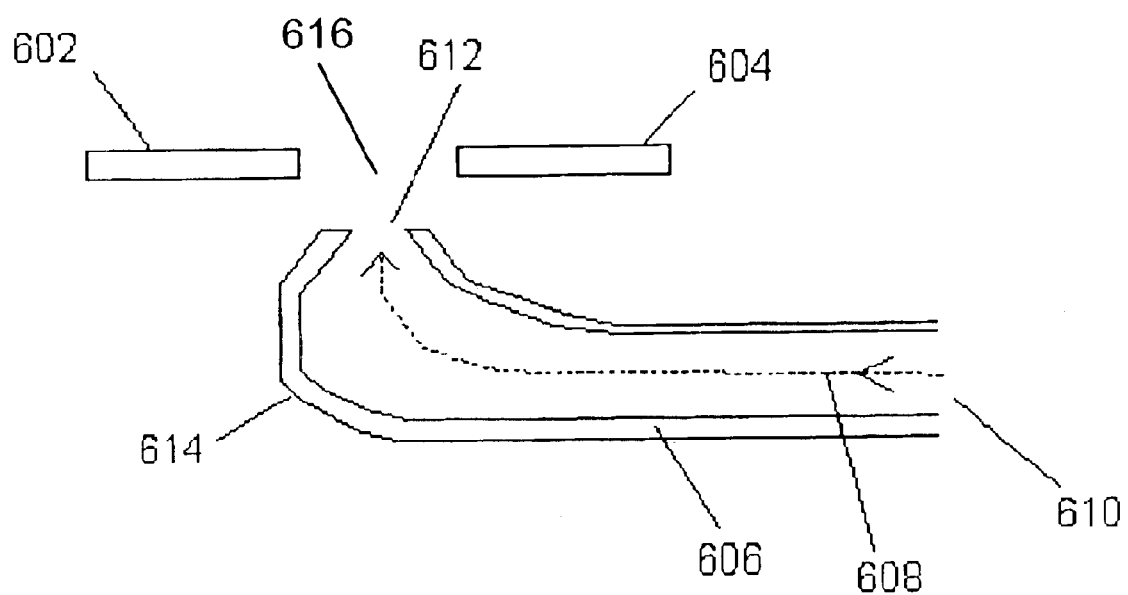
FIG. 19 is a schematic representation of a superconducting nano-channel as a field ionizer.

FIG. 19 is a schematic representation of a superconducting nano-channel as a field ionizer. FIG. 19 illustrates a preferred embodiment in which superconducting nano-channels are used as volcano field ionizers for magnetic nano-particles. Volcano field ionizers make use of a relatively small diameter hollow cathode tube for injecting materials into a region with a very high electric field gradient, which subsequently ionizes the injected materials.

Referring to FIG. 19, superconducting nano-channel 606 is shown having an optional bend region 614. Superconducting nano-channel 606 comprises beam input end 610 and beam exit end (nozzle) 612. A beam of magnetic nano-particles 608 is injected into the superconducting nano-channel 606 through beam input end 610 and exits through nozzle 612. Electrodes 602 and 604 provide a large electrical potential difference between electrodes 602, 604 and nozzle 612. Said large electrical potential difference ionizes magnetic particles 608 in the vicinity of the high electric field region 616 of nozzle 612. Electrodes 602 and 604 may optionally be part of another follow-on superconducting-nano-channel segment.

In another embodiment (not shown), superconducting nano-channels may be used to focus and guide traveling antiprotons for medical applications, such as killing tumors. A suitable liquid nitrogen capillary micro-transport system using a suitable aerogel-based super-insulation may be used for chilling the superconducting nano-channel. Thus, rather than having to use a high energy beam to hit the tumor from multiple angles (which damages other healthy tissue along each such path—i.e. overshoot and undershoot), a single lower velocity beam could be delivered directly to the ultimate target by a thin superconducting nano- or micro-channel probe of the types described elsewhere in this specification. A low velocity beam could be more readily deflected (steered to target) at the tumor site by micro-deflection coils or micro-deflection electrodes than high velocity beams. Since the matter/anti-matter interaction region would thereby be highly localized, so too would the relative density and distribution of (e.g., gamma-ray) radiation of the anti-proton/proton annihilation.

Figure 20A:
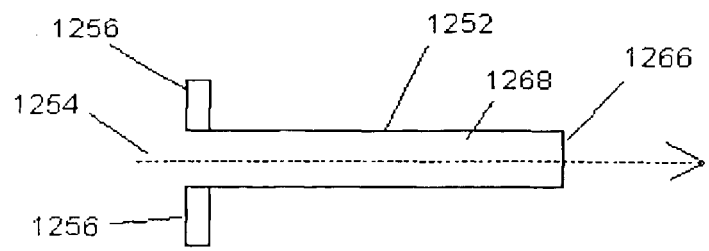
FIGS. 20A–20C are schematic representations of a superconducting nano-channel as a component of an acoustic wave detector system.
Figure 20B:
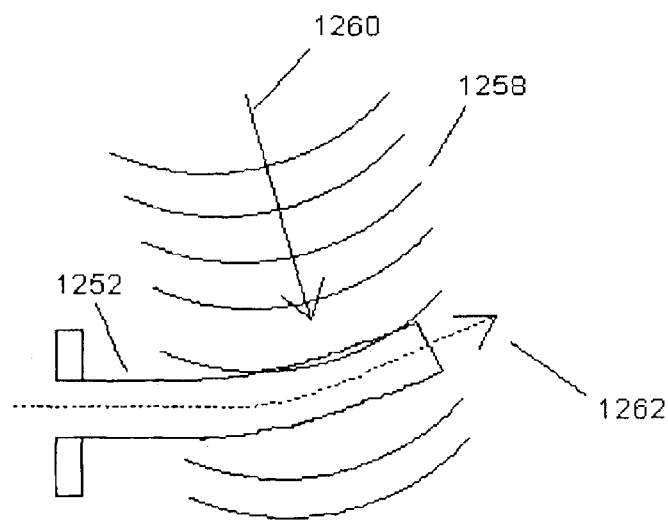
Figure 20C:
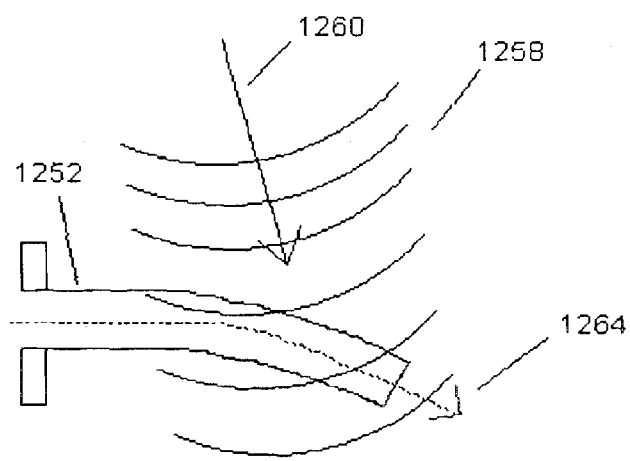

FIGS. 20A–20C are schematic representations of a superconducting nano-channel as a component of an acoustic wave detector system. FIGS. 20A–20C illustrate a preferred embodiment in which superconducting nano-channels may be used as integral components of an acoustic wave detector.

If coherent (i.e. highly monochromatic and well collimated) electron beams or other charged particle beams or magnetic nano or pico-beams are injected into superconducting nano-channels that are deformable by acoustic waves, the acoustic waves produce pronounced perturbations in the electron beams or other charged particle beams or magnetic nano or pico beams as they travel through the superconducting nano-channel. The charged particles exit the superconducting nano-channel in a perturbed state.

Referring to FIG. 20A, charged particle beam 1254 is injected and travels through superconducting nano-channel 1252, which is attached to support 1256. An end cap 1266 is used to cap superconducting nano-channel 1252 and to keep vacuum within region 1268 of superconducting nano-channel 1252. In the absence of acoustic waves, superconducting nano-channel 1252 remains motionless.

Referring to FIGS. 20B and 20C, acoustic wave 1258 propagating in the direction shown by arrow 1260 will cause superconducting nano-channel 1252 to oscillate back and forth, thus deflecting the charged particle beams 1262 and 1264 as they exit superconducting nano-channel 1252. Position sensitive beam detectors (not shown) may be used to detect deflected beams 1262 and 1264 as they exit superconducting nano-channel 1252. These superconducting nano-channel configurations, which take advantage of deflected charged particles, may be used in analog signal processing devices, high-sensitivity and high-bandwidth nano-vibration sensors, pico-beam scanning and chopping operations, and the like. Furthermore, systems comprising superconducting nano-channels, in which deflected charged particles may be modulated, may be suitably mechanically loaded and mechanically driven for generating charged particle scanning patterns.

The superconducting nano-channel structures of this invention, comprising carbon-based nanotubes or other types of nanotubes, may be used with microscopy probes. They may also operate with a miniature ultra-high vacuum enclosure with an electron-transparent widow. Furthermore, these structures may be combined with conventional integrated circuits and micro electro-mechanical fabrication techniques to produce, but not limited to, imaging and detecting devices.

It is, therefore, apparent that there has been provided, in accordance with the present invention, a method and apparatus for guiding and manipulating electron beams or other charged particles. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. A device for guiding a charged particle beam comprising a superconducting nano-channel consisting essentially of a superconducting material in the form of a tube having a proximal end, a distal end, and a bend disposed between said proximal end and said distal end.

2. The device as recited in claim 1, wherein said bend is between zero degrees, and about 180 degrees.

3. The device as recited in claim 1, wherein said bend is about 90 degrees.

4. The device as recited in claim 1, further comprising an electron-transparent window sealed to said distal end of said tube.

5. The device as recited in claim 4, wherein said window is substantially planar.

6. The device as recited in claim 4, wherein said window is a semispherical end cap.

7. The device as recited in claim 4, further comprising an electron beam emitter sealed to said proximal end of said tube.

8. The device as recited in claim 7, wherein said electron beam emitter comprises a first superconducting nanotube.

9. The device as recited in claim 7, wherein said tube, said window, and said electron beam emitter form an ultra-high vacuum region.

10. A device for guiding a charged particle beam comprising a first superconducting nano-channel formed by a substrate, a first area of superconducting material coated on said substrate and having a first edge, a second area of superconducting material coated on said substrate and having a second edge, wherein said first edge of said first area of superconducting material and said second edge of said second area of superconducting material are substantially parallel.

11. The device as recited in claim 10, further comprising a first area of non-conductive material disposed on said first area of superconducting material, and a second area of non-conductive material disposed on said second area of superconducting material.

12. The device as recited in claim 11, further comprising a third area of superconducting material disposed on said first area of non-conductive material, and a fourth area of superconducting material disposed on said second area of non-conductive material.

13. The device as recited in claim 10, further comprising a second superconducting nano-channel formed by said substrate, a third area of superconducting material coated on said substrate and having a third edge, a fourth area of superconducting material coated on said substrate and having a fourth edge, wherein said third edge of third area of superconducting material and said fourth edge of fourth area of superconducting material are substantially parallel.

14. A device for guiding a charged particle beam comprising a superconducting nano-channel formed by a plurality of nano-scale superconducting rods disposed around a central region.

15. The device as recited in claim 14, wherein said plurality of nano-scale superconducting rods is comprised of four rods.

16. The device as recited in claim 14, wherein said plurality of nano-scale superconducting rods is comprised of six rods.

17. The device as recited in claim 16, further comprising a seventh nano-scale superconducting rod disposed in said central region.

18. The device as recited in claim 14, wherein said rods have a substantially circular cross section.

19. A device for guiding a charged particle beam comprising a superconducting nano-channel comprising a first split and a second split disposed parallel to the central axis of said nano-channel, said first and second splits forming a first section and a second section of said nano-channel.

20. The device as recited in claim 19, wherein said superconducting nano-channel is a superconducting nano-cylinder.

21. The device as recited in claim 20, wherein said first split and said second split are parallel.

22. The device as recited in claim 20, wherein said first section and said second sections are half-cylinders.

23. The device as recited in claim 22, wherein said first section comprises a first inner surface, and said second section comprises a second inner surface, and wherein said first section comprise a first layer of conductive material disposed on said first inner surface, and said second section comprise a second layer of conductive material disposed on said second inner surface.

24. The device as recited in claim 20, wherein said first split and said second split are helical.

* * * * *